United States Patent
Barbera-Guillem

(10) Patent No.: US 6,455,310 B1
(45) Date of Patent: Sep. 24, 2002

(54) CELL CULTURE APPARATUS AND METHOD FOR CULTURING CELLS

(75) Inventor: Emilio Barbera-Guillem, Powell, OH (US)

(73) Assignee: BioCrystal Ltd., Westerville, OH (US)

( * ) Notice: Subject to any disclaimer, the term of this patent is extended or adjusted under 35 U.S.C. 154(b) by 0 days.

(21) Appl. No.: 09/526,006

(22) Filed: Mar. 15, 2000

Related U.S. Application Data

(60) Provisional application No. 60/133,415, filed on May 11, 1999, and provisional application No. 60/125,712, filed on Mar. 23, 1999.

(51) Int. Cl.$^7$ .................................................. C12N 5/00
(52) U.S. Cl. .................. 435/383; 435/394; 435/401; 435/402; 435/288.3; 435/288.4; 435/297.1; 435/297.5; 435/305.1; 435/305.2
(58) Field of Search ........................... 435/286.5, 288.3, 435/288.4, 297.1, 297.2, 297.3, 297.5, 305.1, 305.2, 41, 69.1, 383, 394, 401, 402

(56) References Cited

U.S. PATENT DOCUMENTS

| | | | | |
|---|---|---|---|---|
| 4,748,124 A | * | 5/1988 | Vogler | 435/240.241 |
| 5,416,022 A | * | 5/1995 | Amiot | 435/284 |
| 5,523,228 A | | 6/1996 | Ingram et al. | 435/240.25 |
| 5,686,304 A | | 11/1997 | Codner | 435/325 |
| 5,736,398 A | * | 4/1998 | Giambernardi et al. | 435/383 |
| 5,935,847 A | * | 8/1999 | Smith et al. | 435/297.5 |
| 6,110,380 A | | 8/2000 | Barbera-Guillem | 210/695 |
| 6,126,835 A | | 10/2000 | Barbera-Guillem | 210/695 |

* cited by examiner

*Primary Examiner*—David A. Redding
(74) *Attorney, Agent, or Firm*—Raymond A. Miller; Benesch, Friedlander, Coplan & Aronoff, LLP

(57) ABSTRACT

Provided is a cell culture apparatus for culturing cells, and optionally, for performing magnetic separation of cells desired to be cultured. The cell culture apparatus preferably comprises a frame; two membranes, preferably each being gas permeable, which are securedly sealed in a leak-proof selaing to a frame in forming a culture chamber therebetween; and at least one resealable aperture to allow substances to be introduced into, or withdrawn from, the culture chamber.

64 Claims, 5 Drawing Sheets

CELL CULTURE APPARATUS AND METHOD FOR CULTURING CELLS

This is a nonprovisional application based on earlier co-pending applications Ser. No. 60/125,712 filed Mar. 23, 1999, and No. 60/133,415 filed May 11, 1999 which are herein incorporated by reference.

FIELD OF THE INVENTION

The present invention generally relates to an apparatus and methods for growing cells or tissue culture in vitro. More particularly, the present invention relates to a cell culture apparatus containing at least one gas permeable membrane which allows rapid and uniform transfer of gases between the environment of cells contained in the cell culture container apparatus and the atmosphere of the incubator in which the cell culture apparatus is incubated.

BACKGROUND OF THE INVENTION

In eukaryotic cell culture systems, the culture of the cells is generally under conditions of controlled pH, temperature, humidity, osmolarity, ion concentrations, and exchange of gases. Regarding the latter, oxygen and carbon dioxide ($CO_2$) are of particular importance to the culturing of cells. In a typical eukaryotic cell culture system, an incubator is provided in which $CO_2$ is infused to maintain an atmosphere of about 5% $CO_2$ within the incubator. The $CO_2$ interacts with the tissue culture medium, particularly its buffering system, in maintaining the pH near physiologic levels. Conventional cell culture containers comprise tissue culture flasks, tissue culture bottles, and tissue culture plates. Entry of $CO_2$ from the incubator atmosphere into a tissue culture plate generally involves a loosely fitting cover which overhangs the plate in excluding particulate contaminants from entering the plate chamber(s), but allows gas exchange between the incubator atmosphere and the atmosphere within the tissue culture plates. Similarly, for a tissue culture flasks or bottle, a loosely fitting cap excludes particulate contaminants from entering the chamber of the flask or bottle, but allows gas exchange between the incubator atmosphere and the atmosphere within the flask or bottle. More recently, a cap is provided with a gas permeable membrane or filter, thereby allowing for gas exchange with a tightly fitting cap.

In addition to $CO_2$, the culturing of cells is dependent upon the ability to supply to the cells a sufficient amount of oxygen necessary for cell respiration and metabolic function. The supply of oxygen for cell respiration in conventional cell culture containers is in the header space of the container, e.g., the void space in the container that is above the surface of the tissue culture medium. Efforts to increase oxygen concentration to the cultured cells includes mechanical stirring, medium perfusion or aeration, increasing the partial pressure of oxygen, and/or increasing the atmospheric pressure. Thus, in conventional cell culture containers the volume or surface provided for gas exchange, as relative to the volume or surfaces of the whole container, is either inefficiently used and/or results in limiting the rate of gas exchange or in the equilibration of gases. This is even more noticeable in small-scale cultures (15 ml or less) in which rate of cell growth, cell densities, and total cell numbers, are frequently low due to space, surface area, and gas exchange limitations.

The rate of gas exchange across gas permeable membranes has been described as "improved". However, gas permeable membranes have been described as undesirable for use in a cell culture system for various reasons. For example, in U.S. Pat. No. 5,523,228, it is taught that a boundary layer of oxygen toxicity forms at the interface between the gas permeable membrane and the tissue culture medium; and further, cells entering into the toxic boundary layer can be irreparably damaged. Further, in U.S. Pat. No. 5,707,869 it is taught that the chemistry of the surface of gas permeable, liquid impermeable materials is incompatible with many cell types; and additionally, due to their propensity to cause non-specific protein binding, such materials can lead to depletion of soluble growth factors.

Thus, there is a need for a cell culture apparatus that can provide an increased surface area for gas exchange as compared to conventional cell culture containers; and which also provides a high rate of cell growth in achieving a high cell density in a relatively short period of time, and with an even distribution of anchorage dependent cells along the attachment surface.

SUMMARY OF THE INVENTION

The present invention provides a cell culture apparatus comprising at least one frame; two thin membranes wherein at least one of the membranes is gas permeable, and wherein the membranes are securely sealed to (in a leak-proof sealing with) the frame, in forming a culture chamber; and at least one resealable aperture through the frame which allows substances to be introduced into, or withdrawn from, the culture chamber.

In one preferred embodiment, the cell culture apparatus comprises a frame over which is extended and securely sealed thereto two gas permeable membranes in forming a culture chamber therebetween. The frame is sufficiently rigid to provide a housing for assembling the cell culture apparatus of the present invention. The membranes are of suitable thickness to provide sufficient gas permeability to accommodate cell growth in the chamber, and to provide sufficient structural integrity for handling the apparatus. Further, the membranes are of a sufficient optical transparency and clarity so as to observe the cell culture (e.g., the color of the tissue culture medium; and cellular characteristics such as growth and morphology of cells, as observable by microscopy). The frame has at least one resealable aperture, and preferably at least two resealable apertures, which allows substances to be introduced into, or withdrawn from, the culture chamber. Each aperture comprises an opening through the frame which may serve as a passageway into which is guided a portion of an instrument (e.g., needle or pipette or pipette tip) for introducing a substance into or withdrawing a substance from the culture chamber. In a preferred embodiment, the frame is of sufficient thickness and the apertures are of a sufficient limiting diameter to prevent the instrument portion, when inserted through a resealable aperture of the frame, from puncturing either of the walls formed by the membranes of the culture chamber.

In another preferred embodiment, the cell culture apparatus further comprises an additional frame which accommodates the cell culture apparatus formed by the one frame and the two gas permeable membranes. In this embodiment, the cell culture apparatus comprises a two-piece frame comprising an inner frame and an outer frame. The inner frame has securely sealed thereto at least one, and preferably two, gas permeable membranes in forming a culture chamber therebetween. The membranes are of suitable thickness to provide sufficient structural integrity for handling the apparatus. Further, the membranes are of a sufficient optical transparency and clarity so as to observe the cell culture (e.g., the color of the tissue culture medium; and cellular characteristics such as growth and morphology of cells as observable by microscopy). The outer frame has at least one resealable aperture, and preferably at least two resealable apertures, which allows substances to be introduced into, or withdrawn from, the culture chamber (e.g., when aligned with an aperture of the inner frame). The outer frame is a rigid housing shaped to accommodate the insertion and attachment of the inner frame in assembling the cell culture apparatus of the present invention. The inner frame also has at least one aperture, and preferably at least two apertures. Preferably, each aperture of the inner frame is aligned with a resealable aperture of the outer frame in forming aligned apertures. Thus, for example, each aperture of the outer frame may serve as a passageway into which is guided a needle of an instrument for introducing a substance into or withdrawing a substance from the culture chamber. The needle is guided through the aligned (and resealable) apertures of the outer frame and inner frame, and introduced into the culture chamber. In a preferred embodiment, the frame is of sufficient thickness and the apertures are of a sufficient limiting diameter to prevent a needle, when inserted through both a resealable aperture of the outer frame and an aperture of the inner frame with which it is aligned, from puncturing either of the walls comprising the membranes of the culture chamber.

In either embodiment (the one piece frame construction, or the two-piece frame construction), the cell culture apparatus provides an un expected combination of properties including gas exchange and equilibrium, oxygenation of cells cultured in the apparatus, optical transparency and clarity for observing cell culture and cell characteristics during culture, an attachment surface and conditions which promote even distribution of anchorage dependent cells, spatial efficiency, versatility, and conditions which can promote a high rate of cell growth in achieving a high cell density in a relatively short period of time as compared to conventional cell culture devices.

The above and other objects, features, and advantages of the present invention will be apparent in the following Detailed Description of the Invention when read in conjunction with the accompanying drawings in which reference numerals denote the same or similar parts throughout the several illustrated views and embodiments.

DETAILED DESCRIPTION OF THE INVENTION

Definitions

Figure 1:
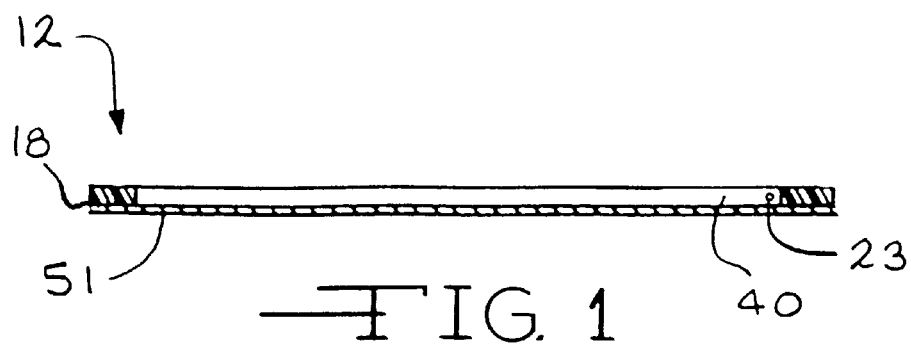
FIG. 1 is a side view of an embodiment of a cell culture apparatus according to the present invention.

The term "gas permeable membrane" is used herein, for the purposes of the specification and claims, to mean a biocompatible material which is liquid impermeable, which is capable of allowing transfer of gases into and out of the cell culture chamber, and which is capable of excluding microbial contamination (e.g., pore size is sufficiently small enough to exclude passage of microbes commonly encountered in contamination of cell cultures), and which has optical transparency and clarity for permitting observation of the cell culture (e.g., of the color of the tissue culture medium which contains a pH indicator; and of cultured cell characteristics such as growth and morphology of the cells as detectable by light microscopy), as will be described in more detail herein. Thickness of the gas permeable membrane will depend on the desired resultant characteristics which may include, but are not limited to, structural integrity, degree of gas permeability, and rate of transfer of gases. In general, the thickness of a gas permeable membrane can range from less than about 0.00125 inches to about 0.005 inches. In a preferred embodiment, the thickness of the membrane is in the range of about 0.0125 inches to about 0.0025 inches. The gas permeable membrane may be comprised of one or more membranes known in the art. Membranes typically comprise suitable polymers that may include polystyrene, polyethylene, polycarbonate, polyolefin, ethylene vinyl acetate, polypropylene, polysulfone, polytetrafluoroethylene, or a silicone copolymer. The choice of the composition of the gas permeable membrane will depend on the type of cell to be cultured (e.g., cells which grow attached (anchorage-dependent), cells which grow in suspension (anchorage-independent), cells that may grow as attached or in suspension), degree of gas permeability, rate of transfer of gases, and optical transparency and clarity. In a preferred embodiment, the gas permeable membrane is comprised of polystyrene. In a more preferred embodiment, the gas permeable membrane is comprised of polystyrene which has been treated, on a side of the membrane which may serve as a surface for attachment of anchorage-dependent cells in culture, by ionization to improve adhesion of the treated membrane surface to anchorage-dependent cells. Ionization of the membrane may render the treated membrane surface more hydrophilic, and can be performed using methods known in the art which include plasma discharge, corona discharge, gas plasma discharge, ion bombardment, ionizing radiation, and high intensity UV light. In a preferred embodiment for promoting growth of anchorage-independent cells, the gas permeable membrane is not treated by ionization.

The term "membrane" is used herein, for the purposes of the specification and claims, to mean either a gas permeable membrane; or a membrane which is incapable of exchanging gas sufficiently to support the growth of cultured cells in the absence of another source for gas exchange ("a non-permeable membrane"). "Membranes" means a gas permeable membrane in combination with either another gas permeable membrane or a non-permeable membrane. A "non-permeable membrane" is a biocompatible material which is liquid impermeable, which is capable of excluding microbial contamination (e.g., pore size is sufficiently small enough to exclude passage of microbes commonly encountered in contamination of cell cultures), and which is optically transparent and clear for permitting observation during the cell culture process. Thickness and/or choice of composition of the non-permeable membrane will depend on the desired resultant characteristics which may include, but are not limited to, structural integrity. In general, the thickness of a non-permeable membrane can range from less than about 0.00125 inches to about 0.009 inches. The non-permeable membrane may be comprised of one or more membranes known in the art. The non-permeable membrane may be treated, on a side of the membrane which may serve as a surface for attachment of anchorage-dependent cells in culture, by ionization to improve adhesion to anchorage-dependent cells.

The term "magnetic-sheet" is used herein, for purposes of the specification and claims, to mean at least one substantially flat sheet having a magnetic field of sufficient strength to attract, and securedly hold into position, magnetic particles (or the a magnetic particle complexed to one or more biological cells) placed adjacent thereto. The magnetic sheet may be substantially stiff (including various degrees of stiffness as known to those skilled in the art), in which case a detachably secured frame (e.g., of the cell culture apparatus according to the present invention) may be removed by pulling the frame apart from the magnetic sheet; or may comprise a flexible magnetic sheet of a sufficient pliability to allow for the magnetic sheet to be separated from a frame to which it is detachably secured by pulling the magnetic sheet apart from frame, as will be more apparent from the following examples. The magnetic sheet may be a magnetized material with alternate north poles and south poles that are linear and parallel. A magnetic sheet includes, but is not limited to, a sheet consisting of a fine magnetic powder such as barium ferrite loaded into a thermoplastic binder; a sheet of plastics or vinyl material impregnated with a ferromagnetic material; a sheet of synthetic resin material having mixed therein a magnetic powder; magnetic particles embedded in a polymer sheet of typically 0.7 mm or 0.030 inches thickness; a vinyl material including magnetic materials dispersed therethrough; or other suitable material having properties compatible with its intended purpose. As apparent to those skilled in the art, the thickness of the magnetic sheet will vary depending on factors which include, but are not limited to, the composition of the sheet material, whether the magnetic sheet comprises one or more sheets, the desired field strength, and the spacing of the magnetic poles. In that regard, and for purposes of illustration but not limitation, the thickness of the magnetic sheet may range from about 0.2 mm to about 5 mm. Illustrative examples of magnetic sheets that can be commercially purchased, and that are useful in making the magnetic separation device according to the present invention, are available under the trademark "PROMAG" (a strontium ferrite-based material) from Magnetic Specialty, Inc., Marietta, Ohio; and a bonded material comprising neodimium, iron, and boron from Electrodyne Co., Inc., Batavia, Ohio. Commercially available examples of a magnetic sheet have a magnetic field strength, as measured by a gaussmeter, in a range which includes, but is not limited to, about 150 to about 600 Gauss.

The term "tissue culture medium" is used herein, for the purposes of the specification and claims, to mean a liquid solution which is used to provide sufficient nutrients (e.g., vitamins, amino acids, essential nutrients, salts, and the like) and properties (e.g., osmolarity, buffering) to maintain living cells (or living cells in a tissue) and support their growth. Commercially available tissue culture medium is known to those skilled in the art.

EXAMPLE 1

Figure 2:
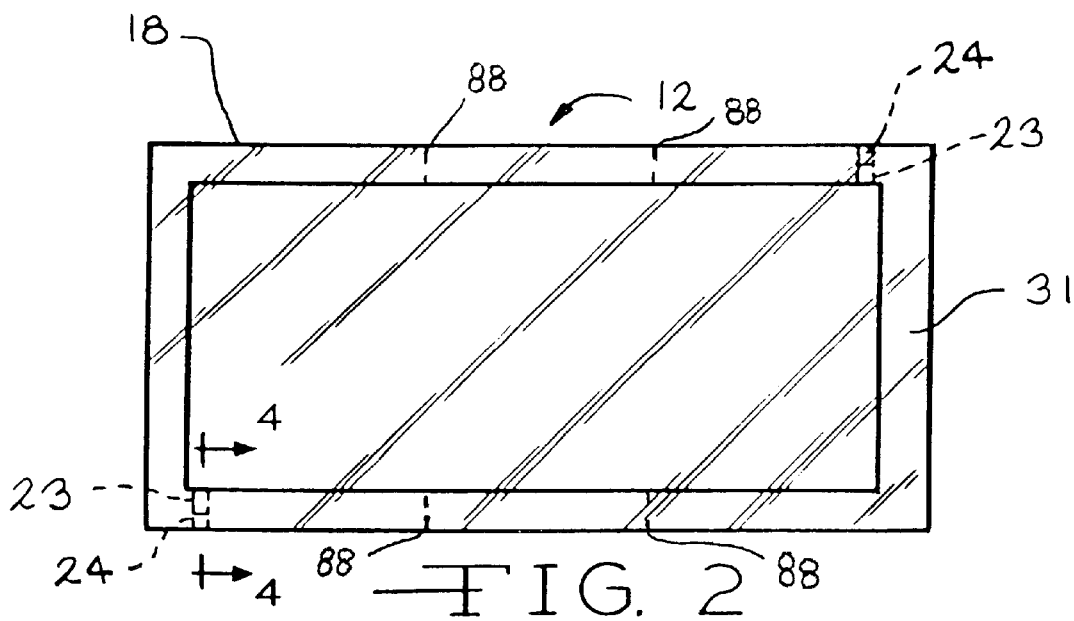
FIG. 2 is a top view of an embodiment of the cell culture apparatus according to the present invention.

In this example, illustrated are various embodiments of the cell culture apparatus according to the present invention. However, in all embodiments of the cell culture apparatus according to the present invention described herein in this Example and the following Examples, an essential feature is that the culture chamber formed therein comprises at least one gas permeable membrane. Referring now to FIGS. 1 & 2, in one embodiment the cell culture apparatus 12 comprises frame 18. Frame 18 may be of a basic biocompatible composition that may comprise suitable plastic, thermoplastic, synthetic, or natural materials which can be fabricated into a framework structure, thereby achieving the required structural integrity for its intended purpose. It should be apparent to those skilled in the art that a wide latitude of choice can be exercised in selecting a material suitable for formation and/or fabrication of frame 18. The dimensions of cell culture apparatus 12, and frame 18, may depend on one or more factors including, but not limited to, the desired fluid capacity of the culture chamber formed therewith, and the dimensions of the culture chamber. In a preferred embodiment, cell culture apparatus 12 is generally rectangular in shape to be able to be accommodated, and be substantially held in position, by a standard mechanical stage specimen holder for a microscope. In a more preferred embodiment, cell culture apparatus 12 (and frame 18) has a length in a range of from about 10 cm to about 13.5 cm, a width in a range of from about 7 cm to about 9 cm, and a height in a range of from about 0.2 cm to about 2.0 cm; or a dimension sufficient to be accommodated, and be substantially held in position, by a standard mechanical stage specimen holder (e.g., that accommodates a 96 well microtiter plate) of a microscope. In a more preferred embodiment, cell culture apparatus 12 has a length of about 12.7 cm, a width of about 8.5 cm, and a height of about 0.5 cm; providing a cell culture apparatus which permits culturing of cells in less incubator space than would be required for culturing cells at a comparable growth rate or to a comparable cell density using a conventional cell culture container.

Referring now to FIGS. 1–7, frame 18 is a housing shaped to accommodate the aligning, contacting and securing thereto (in a leak-proof sealing) membranes 31 & 32 in assembling cell culture apparatus 12 of the present invention. At least one of the two membranes 31 & 32 is a gas permeable membrane; and in a preferred embodiment, both membranes 31 & 32 are gas permeable membranes. Membranes 31 & 32 may be secured to frame 18 in a leak-proof sealing using means that may include mechanical means, chemical means, or other suitable means. For example, a mechanical means such as a non-permanent locking means, clamping mechanism may be used to secure membranes 31 & 32 to frame 18 in forming a leak-proof seal. In another example, chemical means such as the use of an adhesive agent (also encompassing a bonding agent) may be used to secure membranes 31 & 32 to frame 18 in forming a leak-proof seal. The adhesive agent may be in the form of a double-faced adhesive tape, a polymeric adhesive, a pressure-sensitive acrylic adhesive, hot-melt adhesive, rubber cement, or any other form of adhesive or bonding agent useful for the purposes attendant to the present invention. Other suitable means may include one or more of heat bonding, sonic welding, pressure fit sealing in forming a leak-proof seal, and a molding process in which the membranes become an integral part of the frame. For example in using an adhesive agent, the adhesive agent is applied between the frame and the portion of each membrane which is extended over the frame (see, e.g., FIG. 3) such that the portion of the membranes that extend over the frame contacts the adhesive agent on the frame surface, and pressure may be applied to cause a force along the horizontal axis of that portion of the membranes being secured to the frame in a manner which results in a leak-proof sealing between the membranes secured to the frame in the formation of a culture chamber, in a process of assembling the cell culture apparatus according to the present invention.

As will become apparent to one skilled in the art from the description herein, one or more membranes (or a portion thereof) may be removed from frame 18 so as to facilitate further manipulations of cells cultured in the culture chamber of the cell culture apparatus according to the present invention. In one embodiment where anchorage-dependent cells are cultured, and wherein both membranes 31 & 32 are secured to frame 18, a membrane to which is attached the anchorage-dependent cells is removed from the frame by cutting it or peeling it away from the frame. Alternatively, the membrane which is not serving as the attachment surface for anchorage-dependent cells, is cut or peeled from the frame, leaving secured to the frame the membrane to which is attached the anchorage-dependent cells. In either case, the anchorage-dependent cells attached to the membrane may then be directly stained using standard dyes or stains, and methods for staining known to those skilled in the art. For example, the attached cells may be stained for analysis by fluorescence microscopy, phase contrast microscopy, Nomarsky contrast microscopy, scanning electron microscopy, and imaging (e.g., photography or digital imaging) associated therewith. Alternately, the attached cells may be gently scraped off the membrane in circumstances where it is desirable to harvest the cells off of the membrane without enzyme treatment (e.g. trypsinization). Such circumstances may include further use or analysis of the harvested cells where a trypsin-sensitive cell surface molecule is needed to be intact; e.g., for immediate, further analysis such as in flow cytometric analysis, or in a functional bioassay (e.g., cell cytotoxicity assay). As illustrated in FIG. 2, frame 18 may further comprise a plurality of scoring cuts 88 which may facilitate further manipulations of cells cultured in the cell apparatus according to the present invention. These cuts allow for the formation of multiple strips, that may comprise a type of microscopic slide, by breaking along the scoring cuts of the frame having secured thereto a membrane on which is attached anchorage-dependent cells, and cutting the membrane along the plane of the scoring cuts resulting in more than one piece of the frame having attached thereto a strip of membrane.

Figure 4:
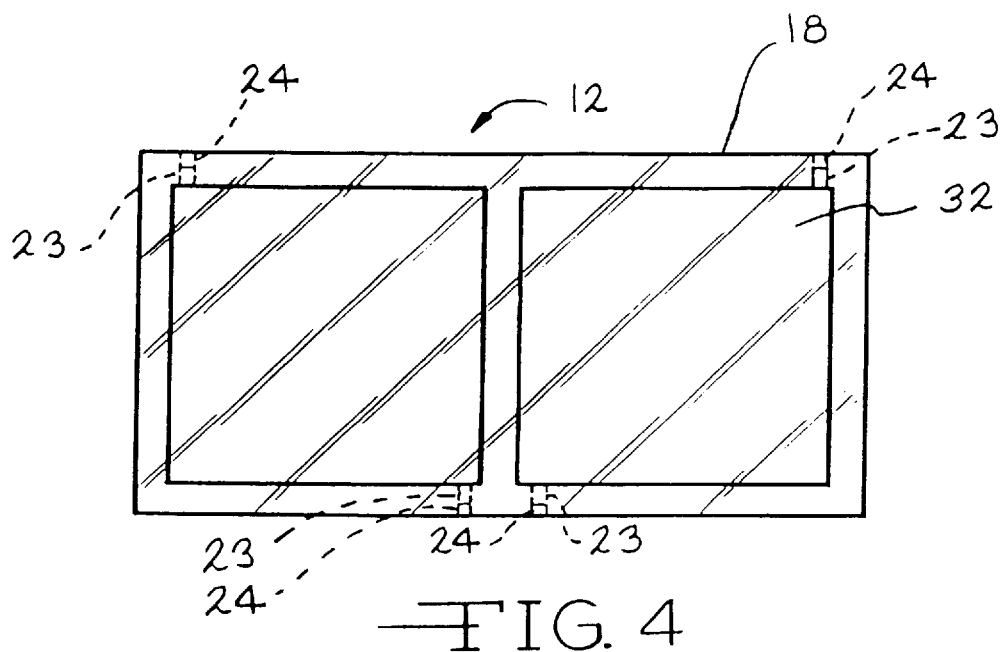
FIG. 4 is a top view of an another embodiment of the cell culture apparatus according to the present invention.
Figure 5:
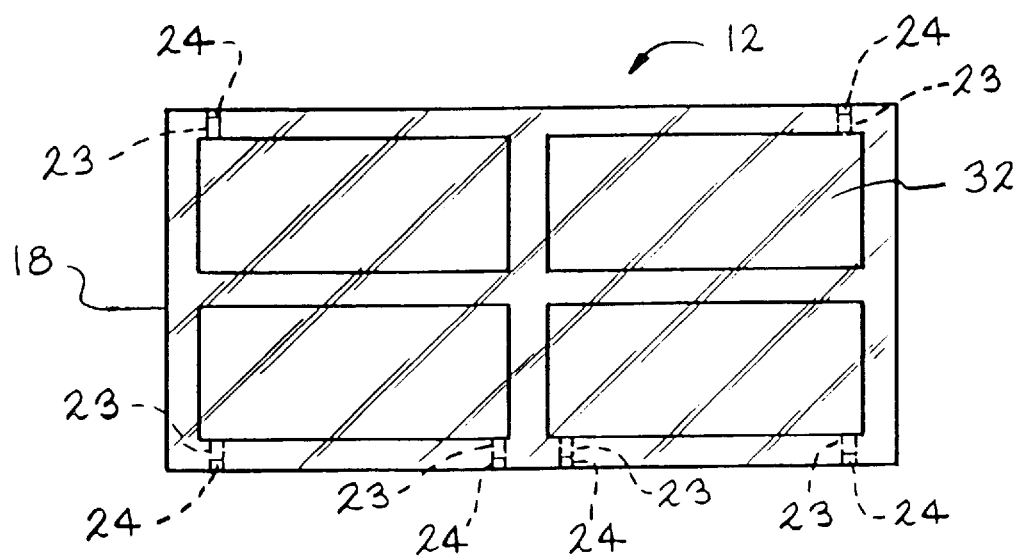
FIG. 5 is a top view of a further embodiment of the cell culture apparatus according to the present invention.
Figure 6:
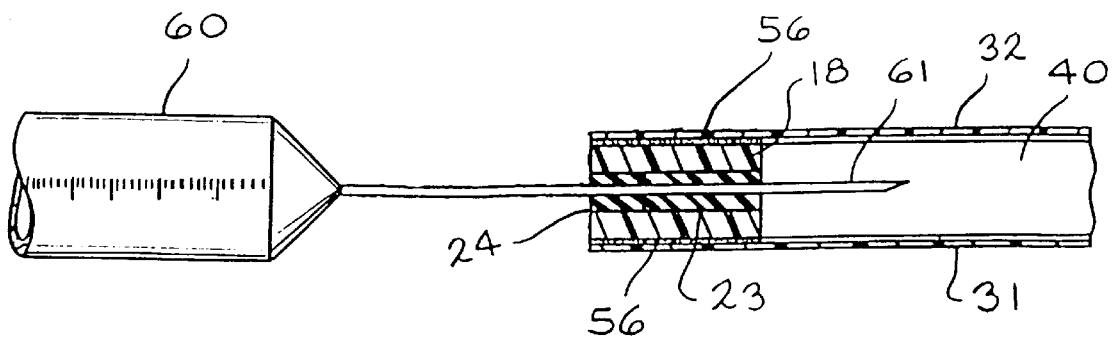
FIG. 6 is a partial cross-sectional view of a cell culture apparatus showing an embodiment wherein a sample is introduced or withdrawn from the culture chamber.
Figure 7:
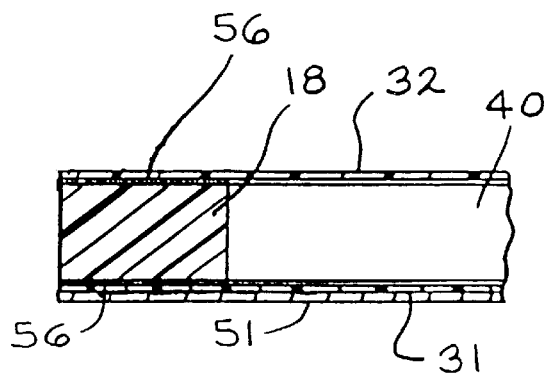
FIG. 7 is a partial cross-sectional view of a cell culture apparatus showing an embodiment wherein a magnetic sheet is detachably secured in a position of contact to the cell culture apparatus.

As shown in FIGS. 2–6, frame 18 has at least one aperture 23, and preferably at least two apertures. As previously described herein, aperture 23 of frame 18 may serve as a passageway into which is guided an instrument for introducing a substance into, or withdrawing a substance from, or venting from, the culture chamber. Thus, the diameter of each aperture 23 is sufficient to allow for entry of that portion of the instrument (for reference purposes only, referred to hereinafter as "tip" of the instrument) which is necessary for its intended purpose of introducing a substance into, or withdrawing a substance from, or venting from, the culture chamber. As will be apparent to one skilled in the art, the diameter of each aperture 23 will depend on the type of instrument being used for the intended purpose, and the size of the tip of the instrument. For example, where the instrument is a syringe and needle assembly, the diameter of each aperture 23 is sufficient to allow a standard needle to pass therethrough (e.g., about 1 mm to about 2 mm in diameter). The tip of the instrument is guided through aperture 23 of frame 18, and introduced into culture chamber 40. In a preferred embodiment, the frame is of sufficient thickness and one or more of apertures 23 are of a sufficient limiting diameter to prevent the tip of the instrument, when inserted through aperture 23, from contacting and puncturing either of the walls of the culture chamber 40 formed by membranes 31 and 32. The at least one aperture 23 is resealable by a suitable means known in the art; e.g., a cap, a plug, or other suitable means. With reference to FIG. 6, and in one preferred embodiment, aperture 23 is substantially filled and sealed with a material comprising gasket 24 that is sufficiently pliable to be self-sealing, thereby allowing for penetration by a needle and resealing after needle withdrawal, in forming a "resealable aperture" 23. Such material is known to those skilled in the art, and may include, but is not limited to one or more of rubber, silicone, silicone-rubber, or other elastomeric material suitable for the intended purpose. In another embodiment, aperture 23 is partially filled and sealed with gasket 24 in forming resealable aperture 23 that allows for penetration by a needle and resealing after needle withdrawal so as to prevent leakage from aperture 23 out of culture chamber 40 of cell culture apparatus 12.

Turning now to the membranes which form the walls of the culture chamber in the cell culture apparatus according to the present invention, in using a gas permeable membrane as an attachment surface in the culture chamber of the cell culture apparatus according to the present invention, it has been observed that anchorage-dependent cells tend to grow relatively uniformly over the entire attachment surface (including the edges of the chamber) during culture. It is believed that this absence of significant variability in cell attachment and growth over the entire attachment surface is due to the relative absence of variability in gas (e.g., oxygen and carbon dioxide) exchange across the length and width of the gas permeable membrane in the culture chamber as provided by the cell culture apparatus according to the present invention. Thus, in the cell culture apparatus according to the present invention, the gas permeable membrane provides an attachment surface which provides for a higher density of, and spatial efficiency for, anchorage-dependent cell growth. This is an advantage over conventional cell culture containers which have been reported to exhibit non-uniform gas exchange over the respective attachment surface; and hence, a variability in the ability of cells to grow depending on their spatial relation to the gradient of gas exchange.

As previously described herein, the membranes may be securedly sealed to the frame by a method that provides a leak-proof sealing. In a preferred embodiment, and in referring now to FIG. 3, a suitable adhesive 56 is interdispersed and cured between membrane 31 and a surface of frame 18, and between membrane 32 and a surface of frame 18 (on an opposing side of frame 18). Adhesives are known to those skilled in the art to include a polymeric adhesive, a pressure-sensitive acrylic adhesive, hot-melt adhesive, rubber cement, solvent-based bonding agent, or any other form of adhesive useful for the purposes attendant to the present invention. As will be apparent to one skilled in the art from the description contained herein, the distance between membrane 31 and membrane 32 depends on the size (e.g., the height) of frame 18. Although there is no general relative restriction on either the shape or size of culture chamber 40, in a preferred embodiment for culturing to achieve a high density of cells, the average distance between membrane 31 and membrane 32 is in a range of from about 1 mm to about 20 mm. In a more preferred embodiment, the average distance between membrane 31 and membrane 32 is about 4 mm.

Figure 3:
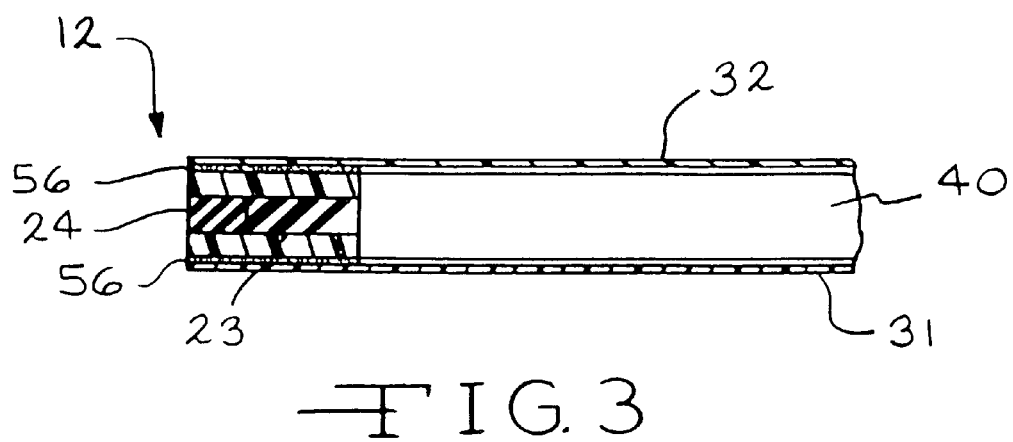
FIG. 3 is a partial cross-section taken through section 4—4 of FIG. 2.

In a preferred embodiment, and in referring to FIG. 3, membrane 31 is a gas permeable membrane which is positioned and securely sealed to a side of frame 18 such that when the cell culture apparatus 12 is incubated in a standard $CO_2$ incubator, membrane 31 is closest of the membranes to the incubator shelf onto which cell culture apparatus is placed. In this preferred embodiment, membrane 31 may be in total or partial physical contact with the incubator shelf. In such a position, and when anchorage-dependent cells are cultured in the cell culture apparatus, membrane 31 serves as the surface to which the anchorage-dependent cells may attach, and is optimally available for uniform gas exchange. In a more preferred embodiment, both membranes 31 and 32 are gas permeable membranes. As will be disclosed in more detail herein, an advantage to having both membranes 31 and 32 comprising gas permeable membranes is the relative uniform gas exchange and equilibrium in the medium and as available to the cultured cells. Additionally, both gas permeable membranes may simultaneously serve as surfaces for attachment of anchorage-dependent cells cultured in the cell culture apparatus according to the present invention. That is, as shown in FIG. 6, anchorage-dependent cells may be introduced into the cell culture apparatus, and the cells introduced are incubated a sufficient time (e.g., minimum of 60 minutes to 4 hours, depending on the cell type) to allow settling by gravity, and attachment to gas permeable membrane 31. The cell culture apparatus may then be rotated 180° so that additional anchorage-dependent cells may be introduced to allow settling by gravity, and attachment to gas permeable membrane 32. In another alternative, anchorage-dependent cells are first introduced to allow settling by gravity, and attachment to gas permeable membrane 32; and then the cell culture apparatus may then be rotated 180° so that additional anchorage-dependent cells may be introduced to allow settling by gravity, and attachment to gas permeable membrane 31. In yet another alternative, anchorage-dependent cells may be introduced into the cell culture apparatus, and the cells introduced are incubated a sufficient time (e.g., minimum of 60 minutes to 4 hours, depending on the cell type) to allow settling by gravity, and attachment of some of the cells to the inner surface of a first gas permeable membrane; and then the cell culture apparatus may be rotated 180° so that unattached anchorage-dependent cells may settle by gravity, and attach to the inner surface of the gas permeable membrane opposite the first gas permeable membrane; in culturing the cells on both membranes which form the walls of the cell culture chamber. Thus, by rotating the cell culture apparatus according to the present invention to allow both membranes 31 and 32 to simultaneously serve as surfaces for attachment of anchorage-dependent cells, provided are spatial efficiency, versatility, and conditions which can promote a high rate of cell growth in achieving a high cell density in a relatively short period of time. In an additional embodiment where primarily only one membrane is used as a surface for attachment, anchorage-dependent cells may be introduced into the cell culture apparatus, and the cells introduced are incubated a sufficient time (depending on the cell type) to allow settling by gravity, and attachment of the cells to gas permeable membrane 31. The cell culture apparatus may then be rotated 180° so that the inverted cells are grown in a culture as suspended from membrane 31.

Both membranes 31 & 32 are of a sufficient optical transparency and clarity so as to permit observation during culture, such as of the color of the tissue culture medium, and of cellular characteristics (e.g., growth and morphology of cells such as by microscopy). More particularly, diffusion of $CO_2$ into tissue culture medium having a pH indicator, whether from placing the cell culture apparatus into an incubator and/or as cultured cells produce the gas, changes the color of the medium's pH indicator (typically ranging from an initial dark pink to a reddish orange to an orangish color). Membranes 31 & 32 are of a sufficient optical transparency and clarity so as to observe during culture, changes in the color of the medium's pH indicator. Additionally, both membranes 31 & 32 are of a sufficient optical transparency and clarity so that when cell culture apparatus is placed onto a microscope stage for analysis, the cultured cells therein may be visually analyzed for cell shape, cell number, and additional cell characteristics that typically can be observed by light microscopy.

In alternative embodiments of the cell culture apparatus according to the present invention, there are multiple culture chambers. In a more preferred alternative embodiment of the cell culture apparatus having multiple culture chambers, the number of culture chambers is a number ranging between 2 and 10. Now referring to FIGS. 2, 4 & 5, provided is a top view of frame 18 with one culture chamber, two cell culture chambers, and four culture chambers formed therein, respectively. In a cell culture apparatus having multiple culture chambers, one membrane 31 and one membrane 32 may be extended over and securedly sealed onto opposites sides of frame 18, and along any portion of frame 18 that serves to divide the frame for formation of multiple culture chambers, in forming the multiple culture chambers. It is also embodied that each culture chamber could be formed by its own membrane 31 and membrane 32; however, that would require frame 18 to have multiple membranes 31 and multiple membranes 32 sealed thereto. It is also shown in FIGS. 4 & 5 that each cell culture chamber has at least one aperture 23; and in a more preferred embodiment, has two apertures 23. As previously described herein, desirably each aperture 23 is resealable. With reference again to FIG. 4, where there are two apertures 23 per culture chamber, it may be desirable to have a first aperture 23 located at one end of the culture chamber, and a second aperture 23 located at the opposite end of the culture chamber. Such an arrangement may facilitate processes like venting the chamber, and removing air bubbles from the chamber. For purposes of illustration, but not limitation, and wherein cell culture apparatus 12 has a length of about 12.7 cm, a width of about 8.5 cm, and a height of about 0.4 cm, each of the two chambers illustrated in FIG. 4 would hold about 2.5 to about 7.5 ml of tissue culture medium; and each of the four chambers illustrated in FIG. 5 would hold about 1.25 to about 3.75 ml of tissue culture medium.

In an additional embodiment, a bioreactor comprises a plurality of the cell culture apparatuses according to the present invention which are operatively linked by providing a fluid passageway connecting the culture chambers of the plurality of cell culture apparatuses. To facilitate culturing of cells in such a bioreactor environment, each of the plurality of the cell culture apparatuses may be interconnected with another cell culture apparatus by a connecting passageway that allows for the flow of tissue culture medium through the passageway and between the culture chambers of the interconnected cell culture apparatuses. One example of interconnecting a first cell culture apparatus to a second cell culture apparatus in forming a bioreactor is by the use of a piece of sterile tubing interposed between two syringe needles. One needle would be inserted into a resealable aperture 23, through the frame, and into a culture chamber of the first cell culture apparatus; and the second needle would be inserted into a resealable aperture 23, through the frame, and into a culture chamber of a second cell culture apparatus. A piece of tubing may then have one open end operatively connected to the first needle, and the opposite open end of the tubing operatively connected to the second needle. The tubing, located between and operatively connected to the two needles, provides fluid flow communication between the culture chamber of the first cell culture apparatus and the culture chamber of the second cell culture apparatus. Using similar methodology and a plurality of tubing, a plurality of the cell culture apparatuses may be operatively connected in forming a bioreactor.

EXAMPLE 2

In this example, illustrated is another embodiment of the cell culture apparatus according to the present invention. In this embodiment, and with reference to FIGS. 8 & 9, the cell culture apparatus 12 further comprises outer frame 16 in forming a two-piece frame comprising outer frame 16 and frame 18. Various embodiments of frame 18 and membranes 31 & 32 have been previously described in detail in Example 1, and illustrated in FIGS. 1–7. Outer frame 16 may be of a basic biocompatible composition that may comprise suitable plastic, thermoplastic, synthetic, or natural materials which can be fabricated into a framework structure, thereby achieving the required structural integrity for its intended purpose. The dimensions of cell culture apparatus 12, and outer frame 16 and frame 18, may depend on one or more factors including, but not limited to, the desired fluid capacity of the culture chamber formed therewith, and the dimensions of the culture chamber. In a preferred embodiment, cell culture apparatus 12 is generally rectangular in shape to be able to be accommodated, and be substantially held in position, by a standard mechanical stage specimen holder for a microscope. In a more preferred embodiment, cell culture apparatus 12 (and outer frame 16) has a length in a range of from about 10 cm to about 13.5 cm, a width in a range of from about 7 cm to about 9 cm, and a height in a range of from about 0.5 cm to about 2.0 cm; or a dimension sufficient to be accommodated, and be substantially held in position, by a standard mechanical stage specimen holder (e.g., that accommodates a 96 well microtiter plate) of a microscope. In a more preferred embodiment, cell culture apparatus 12 (and outer frame 16) has a length of about 12.7 cm, a width of about 8.5 cm, and a height of about 1 cm; providing a cell culture apparatus which permits culturing of cells in less incubator space than would be required for culturing cells at a comparable growth rate or to a comparable cell density using a conventional cell culture container. In a more preferred embodiment, frame 18 has a length in a range of from about 4 cm to about 11.5 cm, a width in a range of from about 4 cm to about 7.5 cm, and a height in a range of from about 0.2 cm to about 0.8 cm. In a most preferred embodiment, frame 18 has a length of about 11 cm, a width of about 6 cm, and a height of about 0.3 cm.

Referring now to FIGS. 9–12, outer frame 16 is a rigid housing shaped to accommodate the alignment, contact and securing of frame 18 (having secured thereto, in a leak-proof sealing, membranes 31 & 32) thereto in assembling cell culture apparatus 12 of the present invention. Securing of frame 18 to outer frame 16 requires that a leak-proof seal be formed at least where an aperture 23 of frame 18 meets with and is aligned with an aperture 21 of outer frame 16 in forming aligned apertures 21 and 23, wherein at least one of the apertures of the aligned apertures is resealable. In one embodiment, frame 18 (having secured sealed thereto membranes 31 & 32) is fitted into a recessed portion of outer frame 16 (see, e.g., FIG. 9), and then frame 18 and outer frame 16 are permanently secured together by a means of sonic welding, bonding, adhesive, or other suitable means known in the art for this intended purpose. Securing together of outer frame 16 and frame 18 may comprise contacting and securing of outer frame 16 to frame 18; contacting and securing of outer frame 16 to a membrane (e.g., either membrane 31 or membrane 32) which is securely sealed to frame 18; and a combination thereof.

In another embodiment, frame 18 (having securedly sealed thereto membranes 31 & 32) is fitted into a recessed portion of outer frame 16 (see, e.g., FIG. 9), and frame 18 is then detachably secured to outer frame 16 in a non-permanent manner. Means to detachably secure frame 18 to outer frame 16 may include mechanical means, chemical means, or other suitable means. For example, a mechanical means such as snap-fitting, pressure fitting, a non-permanent locking means, clamping mechanism, or a tongue and groove fitting arrangement, may be used to detachably secure frame 18 to outer frame 16 in forming a leak-proof seal. In another example, chemical means such as the use of a non-permanent adhesive or non-permanent bonding agent may be used to detachably secure frame 18 to outer frame 16 in forming a leak-proof seal. The non-permanent adhesive or non-permanent bonding agent may be in the form of a double-faced adhesive tape, a polymeric adhesive, a pressure-sensitive acrylic adhesive, hot-melt adhesive, rubber cement, or any other form of adhesive or bonding agent useful for the purposes attendant to the present invention. Detachably securing together of outer frame 16 and frame 18 may comprise contacting and securing of outer frame 16 to frame 18; contacting and securing of outer frame 16 to a membrane (e.g., membrane 31 or membrane 32) which is securely sealed to frame 18; and a combination thereof. In another embodiment of detachably securing frame 18 with outer frame 16, outer frame 16 has secured thereto, in a recessed portion into which is eventually fitted frame 18, one membrane (either membrane 31 or 32) in a leak-proof sealing. Outer frame 16, with the membrane so attached, is then contacted, fitted, and secured with frame 18 having attached thereto in a leak-proof sealing the second membrane so as to form a culture chamber, wherein the second membrane is on the side of the frame 18 opposite to that positioned in and contacted and secured with outer frame 16. Pressure may be applied to cause a downward force along the horizontal axis of the outer frame in locking frame 18 into a recessed portion of the outer frame in a manner to be detachably secured, and to result in a leak-proof sealing between the outer frame and frame 18 and the formation of a culture chamber, in a process of assembling the cell culture apparatus according to the present invention. Detachably securing together of outer frame 16 and frame 18 may comprise contacting and securing of outer frame 16 to frame 18; contacting and securing of the membrane, which is securedly sealed to outer frame 16, to frame 18; and a combination thereof.

As will become apparent to one skilled in the art from the description herein, detachably securing frame 18 to outer frame 16 may facilitate further manipulations of cells cultured in the culture chamber of the cell culture apparatus according to the present invention. In one embodiment where anchorage-dependent cells are cultured, and wherein both membranes 31 & 32 are secured to frame 18, frame 18 may be removed from outer frame 16. A membrane, to which is attached the anchorage-dependent cells, is removed from the inner frame by cutting it or peeling it away from the inner frame. Alternatively, the membrane which is not serving as the attachment surface for anchorage-dependent cells, is cut or peeled from frame 18, leaving secured to frame 18 the membrane to which is attached the anchorage-dependent cells. In either case, the anchorage-dependent cells attached to the membrane may then be directly stained using standard dyes or stains, and methods for staining known to those skilled in the art; or otherwise removed or manipulated (as previously described in detail in Example 1). Likewise, in the assembly wherein one membrane is secured to the outer frame and the other membrane is secured to frame 18, and the outer frame and frame 18 are detachably secured in forming the cell culture apparatus, after culturing cells in the cell culture apparatus frame 18 may be removed from the outer frame. Whichever membrane (or both) that has attached thereto the cultured cells may be used as a substrate (whether still attached to the respective frame, or separated therefrom) on which the attached cells are further manipulated (e.g., staining, observed, imaged, harvested by gentle scraping, used in a functional assay, etc.). In a further embodiment, either the outer frame, frame 18, or a combination thereof, may further comprise scoring cuts across the respective frame. The scoring cuts may facilitate further manipulations of cells cultured in the cell apparatus according to the present invention including one or more of: removing outer frame from frame 18; facilitating access and handling of a membrane having attached thereto anchorage-dependent cells; facilitating removal of tissue culture medium and/or cultured cells (e.g., whether anchorage-dependent or anchorage-independent); and forming multiple strips, that comprise a type of microscopic slide, by breaking along the scoring cuts a frame having secured thereto a membrane on which is attached anchorage-dependent cells, and cutting the membrane along the plane of the scoring cuts resulting in more than one piece of the frame having attached thereto a strip of membrane.

Figure 8:
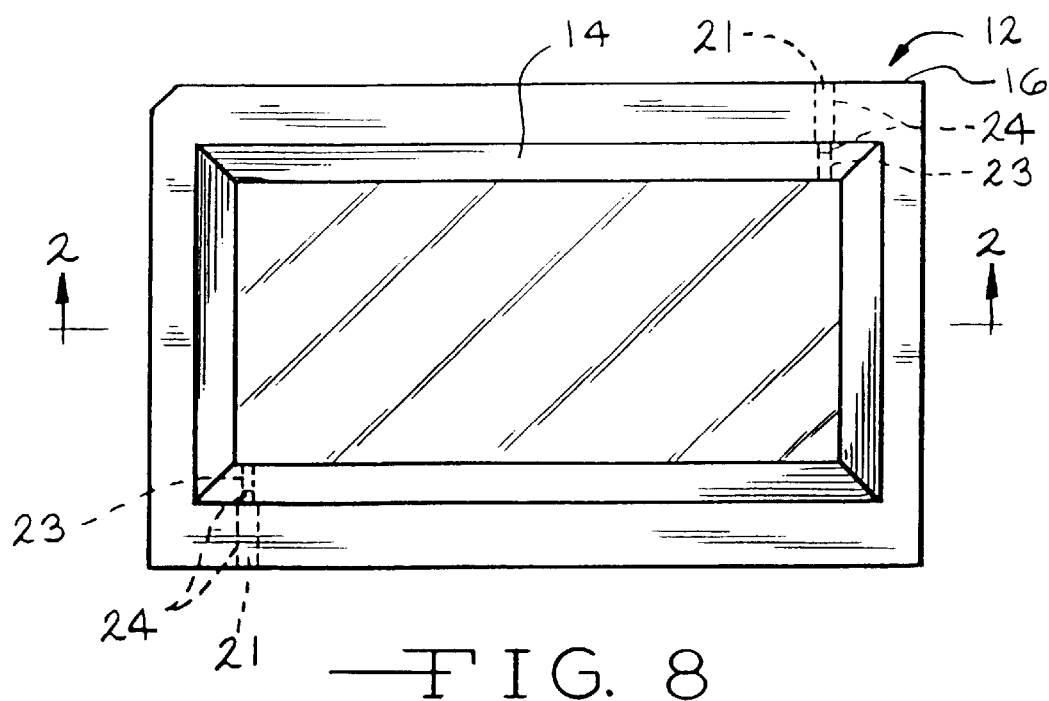
FIG. 8 is a top view of another embodiment of the cell culture apparatus according to the present invention.
Figure 10:
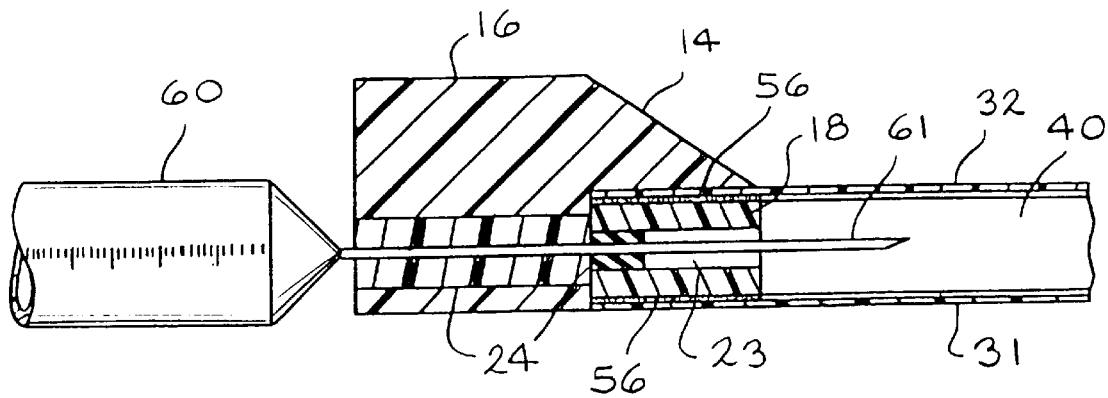
FIG. 10 is a partial cross-sectional view of a cell culture apparatus showing an embodiment wherein a sample is introduced or withdrawn from the culture chamber.
Figure 11:
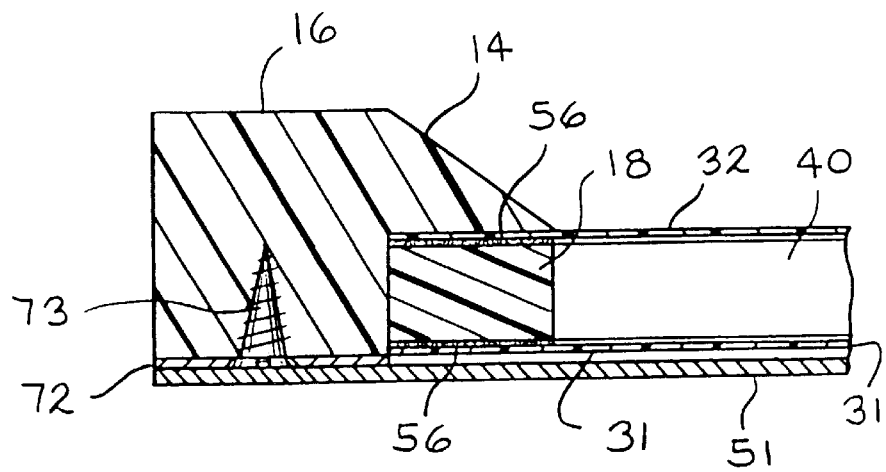
FIG. 11 is a partial cross-sectional view of a cell culture apparatus showing an embodiment wherein a metal frame is secured to the outer frame, and a magnetic sheet is held in position by magnetic attraction to the metal frame.

As shown in FIGS. 8 and 10, outer frame 16 has at least one aperture 21, and preferably at least two apertures. At least one aperture 21 of outer frame 16 is aligned with at least one aperture 23 of frame 18 in forming aligned apertures, wherein at least one of the apertures of the aligned apertures is resealable. Thus, for example, aperture 21 of the outer frame may serve as a passageway into which is guided a needle for introducing a substance into, or withdrawing a substance from, or venting from, the culture chamber. Thus, the diameter of each of aperture 21 and aperture 23 is that it is sufficient to have a standard needle pass therethrough (e.g., about 1 mm to about 2 mm in diameter). The needle is guided through aligned apertures 21 (of outer frame 16) and 23 (of frame 18), and introduced into culture chamber 40. In a preferred embodiment, the frame is of sufficient thickness and one or more of apertures 21 and 23 are of a sufficient limiting diameter to prevent a needle, when inserted through aligned apertures 21 and 23, from contacting and puncturing either of the walls of the culture chamber 40 formed by membranes 31 and 32. With reference to FIG. 10, in one preferred embodiment, aperture 21 is substantially filled and sealed with a material comprising gasket 24 that is sufficiently pliable to be self-sealing, thereby allowing for penetration by a needle and resealing after needle withdrawal, in forming a "resealable aperture" 21. Such material is known to those skilled in the art, and may include, but is not limited to one or more of rubber, silicone, silicone-rubber, or other elastomeric material suitable for the intended purpose. In another embodiment, aperture 21 is partially filled and sealed with gasket 24 in forming resealable aperture 21 that allows for penetration by a needle and resealing after needle withdrawal so as to prevent leakage from aperture 21 out of culture chamber 40 of cell culture apparatus 12. In a further embodiment, in aligned apertures 21 and 23, aperture 21 is filled and sealed with gasket 24 and aperture 23 is partially filled or substantially filled in a manner that allows for penetration by a needle and resealing after needle withdrawal so as to prevent leakage out of cell culture apparatus 12 from aligned apertures 21 and 23, in forming resealable aperture 21 and resealable aperture 23.

Figure 9:
FIG. 9 is a side view taken along line 2—2 of FIG. 8.

In a more preferred embodiment, and in referring to FIGS. 8 & 9, a beveled portion 14 of outer frame 16 slopes at about a 35° angle in relation to the plane of the at least one gas permeable membrane. This angling or beveling of portion 14 is an advantage in that when using cell culture apparatus 12, observed are an attachment surface and conditions which promote an even distribution of anchorage-dependent cells across the entire surface of the membrane to which the cells are attached in culture chamber 40. Thus, to adequately view with a microscope the cells in the cell culture apparatus which grow at the edges of cell chamber 40, and because standard microscope objective lens are beveled at the tip at about a 35° angle in relation to the mechanical stage, portion 14 allows a user to position a standard microscope objective lens in a manner to permit the user to adequately view such cells. In that regard, and as described in more detail in Example 1 herein, use of a gas permeable membrane as an attachment surface in the culture chamber of the cell culture apparatus according to the present invention generally results in an unexpected absence of significant variability in cell attachment and growth over the entire attachment surface. Although there is no general restriction on either the shape or size of culture chamber 40, in a preferred embodiment for culturing to achieve a high density of cells, the average distance between membrane 31 and membrane 32 is (i.e., the membranes are spaced apart by a distance) in a range of from about 1 mm to about 5 mm. In a more preferred embodiment, the average distance between membranes 31 and 32 is about 3 mm.

In a preferred embodiment, and in referring to FIG. 10, membrane 31 is not in physical contact with the incubator shelf, but a portion of outer frame 16 is in physical contact with the incubator shelf when the cell culture apparatus 12 is incubated in a standard $CO_2$ incubator (i.e., there is a space between membrane 31 and the incubator shelf). This arrangement also allows for more than one cell culture apparatus to be stacked while still maintaining a space which allows for gas exchange substantially across the width and length of each respective membrane 31. In a more preferred embodiment, both membranes 31 and 32 are gas permeable membranes, having advantages such as those previously described in more detail in Example 1. In alternative embodiments of the two-frame construction of the cell culture apparatus according to the present invention, and as previously described in more detail in Example 1, frame 18 may comprise multiple culture chambers. In an additional embodiment wherein the cell culture apparatus may comprise more than one culture chamber, the outer frame may be fashioned (e.g., by a series of grooves or recessed portions) to accommodate more than one frame 18 (with each frame 18 comprising at least one culture chamber); and the cell culture apparatus is comprised of an outer frame in which are accommodated and secured therein more than one frame 18. Thus, the cell culture apparatus may serve as a bioreactor comprised of a plurality culture chambers. The plurality of culture chambers may interconnected to allow for the flow of tissue culture medium therebetween, such as by the use of sterile tubing interposed between two syringe needles, as previously described in more detail in Example 1. For example one needle would be inserted into aligned apertures 21 and 23 and into a culture chamber of a first cell culture apparatus comprising frame 18; and the second needle would be inserted into aligned apertures 21 and 23 and into a culture chamber of a second cell culture apparatus comprising frame 18. The tubing, located between and operatively connected to the two needles, provides fluid flow communication between a culture chamber of a first frame 18 and the culture chamber of the second frame 18. Using similar methodology and a plurality of tubing, a plurality of frames 18 may be operatively connected in forming a bioreactor.

EXAMPLE 3

In this example, illustrated are various embodiments of using the cell culture apparatus according to the present invention to culture cells, whether the cells are individual cells (cells which are grown independent of forming a structure such as a tissue; an illustrative example being a cell line), or cells forming a tissue (typically, a mesh or network of cells, with their intercellular substance in forming a structured or organized tissue), or a combination thereof. It will be apparent to one skilled in the art that individual cells which can be cultured in the cell culture apparatus comprise one or more cell types including, but not limited to, animal cells, insect cells, mammalian cells, human cells, transgenic cells, genetically engineered cells, transformed cells, cell lines, anchorage-dependent cells, and anchorage-independent cells. It will be also apparent to one skilled in the art, that tissue formed by cells in culture can also be cultured in the cell culture apparatus according to the present invention. It will further be apparent to one skilled in the art that the cell culture apparatus of the present invention is generally not limited to a specific type of cell to be cultured, nor the tissue culture medium capable of sustaining cell growth as long as the medium provides sufficient nutrients and properties (e.g., osmotic pressure) to maintain and support cell growth.

In one embodiment, anchorage-dependent cells are cultured in the cell culture apparatus according to the present invention. For growing anchorage-dependent cells, at least one of the membranes of the culture chamber has an inner face which comes in contact with the cells, and which is of sufficient hydrophilicity for promoting adhesion of cells desire to be cultured; and therefore, can act as a surface to which the cells can attach and grow. The at least one membrane may have inherent chemical properties which promote such adhesion, or the inner face may be treated (e.g., electrically, ionically, or chemically) to promote such adhesion. It will be apparent to one skilled in the art that such treatment may include one or more of chemically etching of the inner surface, ionization of the inner surface, or coating the inner surface with a suitable coating reagent. Suitable coating reagents are known to those skilled in the art to include gelatin, collagen, fibronectin, an adhesion protein, an adhesion peptide (see, e.g., PCT/US95/00817).

A method of culturing cells using the cell culture apparatus according to the present invention comprises suspending the cells to be cultured (e.g., anchorage-dependent cells or anchorage-independent cells) in an appropriate amount of tissue culture medium to support cell growth, in forming a suspension; introducing the suspension into a suitable instrument (e.g., a syringe and needle combination) for injecting the suspension into the cell culture apparatus; using sterile (aseptic) technique, and inserting a portion (e.g., the tip of a needle) of the instrument through a resealable aperture and into the cell culture chamber of the cell culture apparatus (or with respect to a cell culture apparatus further comprising an outer frame, through a set of aligned apertures; e.g., comprising a resealable aperture 21 and a correspondingly aligned aperture 23); expelling the suspension from the instrument (e.g., from the chamber of a syringe and through the tip of the needle) and into the cell culture chamber; withdrawing the portion (e.g., the tip of the needle) of the instrument from the cell culture apparatus; and incubating the cell culture apparatus, containing the suspension of medium and cells, in a cell culture incubator (the incubator providing conditions sufficient for cell growth as known in the art; e.g., a closed environment with controlled atmospheric conditions including suitable temperature and $CO_2$ concentration).

It is noted here that the steps of introducing the cells and medium into the cell culture apparatus according to the present invention can be performed in a sterile environment, or non-sterile environment provided that aseptic technique is used. This is because the cell culture apparatus itself (when sterilized using conventional means known in the art) can provide a sterile, hermetic environment. With respect to aseptic technique, and as an illustrative example, gasket 24 may be first wiped with alcohol, and then sterile needle 61 of syringe 60 (containing a suspension of cells to be culture) is inserted through the aperture (as shown in FIG. 6) or series of aligned apertures (e.g., as shown in FIG. 10) with the resultant introduction of needle 61 into culture chamber 40. The suspension of cells may then be expelled from syringe 60, through needle 61, and into culture chamber 40. Needle 61 may then be withdrawn from cell culture apparatus 12, and upon its withdrawal, the puncture caused by needle 61 is spontaneously sealed by the gasket 24 to prevent leakage from cell culture chamber 40.

There are multiple ways for introducing one or more substances into the culture chamber of the cell culture apparatus. It will be apparent to those skilled in the art that a substance that may be introduced into the culture chamber of the cell culture apparatus may include one or more of tissue culture medium alone, tissue culture medium with cells, cells suspended in a physiological buffer, and a drug or cytokine or growth factor or enzyme (e.g., solution of trypsin) or other biological agent to treat cells cultured therein. Depending on factors such as the amount of substance introduced into the cell culture chamber, and the size of the aperture, it may sometimes be necessary to provide venting of the culture chamber. Thus, the step of introducing a suspension of cells, in the method of culturing cells in the cell culture, may further comprise a venting step. Venting is a process in which air or gas is allowed to be displaced from the culture chamber when the substance is introduced into the culture chamber. Venting may be necessary to relieve pressure on the membranes of the cell culture chamber caused by the injection of air during the process of introducing the substance into the culture chamber. In one embodiment, the same resealable aperture 23 is utilized for both introducing the substance into the culture chamber, and for allowing air or gas to be withdrawn from the culture chamber. In an example, a portion of the substance is introduced into the culture chamber, and then the syringe and needle containing the remaining substance to be introduced is withdrawn from the cell culture apparatus. The cell culture apparatus is then tilted or rotated until the air or gas bubble (collectively referred to as "bubble") is in the proximity of the same aperture 23. A second syringe and needle, the syringe being empty, is inserted into the same aperture 23 such that the tip of the needle is inside the bubble; and then the syringe plunger may be pulled back to remove the bubble from the culture chamber in a process of venting the culture chamber. The second syringe and needle may then be removed from the aperture 23, and the first syringe and needle containing the remaining substance to be introduced may then be re-inserted into and through the same aperture to introduce the remainder of the substance into the culture chamber. As will be apparent to one skilled in the art, and depending on the amount of substance to be introduced or whether a bubble is desirable or the size of the culture chamber, there can be multiple alternations between the first syringe and needle and the second syringe and needle.

In an alternative embodiment, more than one aperture is utilized for introducing the substance into the culture chamber, and for allowing air or gas or a solution (e.g., culture medium) to be displaced from the culture chamber. In an example of using more than one aperture, inserted into a first aperture 23 is a needle connected to a syringe containing the substance to be introduced into the culture chamber. Inserted into a second aperture 23, which provide access to the same culture chamber as the first aperture 23, is a second needle, wherein the second needle may be a needle alone (without connection to a syringe). The cell culture apparatus is rotated or tilted in a manner so that when the substance is slowly introduced into the culture chamber using the syringe and needle inserted through the first aperture, gas or air is expelled through the second needle inserted in the second aperture in a process of venting the culture chamber. After the substance is introduced into the culture chamber, the syringe and needle may be removed from the first aperture, and the second needle can be removed from the second aperture. This process of venting may be facilitated by spacing apart the first aperture from the second aperture, such as at opposite ends of the cell culture chamber and cell culture apparatus, as illustrated in FIGS. 2, 4, and 8.

In an embodiment comprising a method of harvesting one or more substances present in the medium of cells cultured in a cell culture apparatus according to the present invention, inserted into a first aperture is a needle connected to a bag or similar container having a controlled delivery device (e.g., drip-control as in an i.v. bag for intravenous administration) and containing the fresh tissue culture medium to be introduced into the culture chamber. Inserted into a second aperture, which provides access to the same culture chamber as the first aperture, is a second needle. The second needle may be connected to one end of a piece of tubing, wherein the opposite end of the tubing is introduced into or connected to a collection vessel. Thus, as the fresh tissue culture medium is dripped into the culture chamber of the cell culture apparatus, displaced through the second aperture and collected from the culture chamber of the cell culture apparatus may be culture medium from cultured cells containing cell products released during culture (e.g., in a method for harvesting monoclonal antibodies from hybridoma cells, or a method of harvesting recombinant proteins from transfected cells).

In a preferred embodiment, and for applications in which a high growth rate of cells is desired, in a method of culturing cells in the cell culture apparatus according to the present invention, the cell culture chamber may be filled completely with tissue culture medium or other suitable growth medium for culturing cells or tissue desire to be grown. It will be apparent to one skilled in the art that completely filling the culture chamber means that there is substantially no head space remaining in the culture chamber. It is noted that there can be an abrupt, initial rise in the pH of tissue culture medium within the first hour or two in conventional cell culture containers due mainly to the distribution of dissolved $CO_2$ between the medium and the gas phase. This pH change has mostly occurred within the first hour of incubation, well before cells are capable of producing significant amounts of $CO_2$. The resultant pH change negatively effects the rate of cell growth until the cells are in sufficient number to restore the optimal $CO_2$ level by providing $CO_2$ through cell respiration. However, unlike the conventional cell culture containers, the cell culture apparatus according to the present invention can be filled in a manner wherein a substantial head space is lacking. Further, the cell culture apparatus of the present invention provides an unexpected capacity for gas equilibrium believed to be due to the enhanced gas exchange exhibited by the use and arrangement of one or more gas permeable membranes. Together, these features of the cell culture apparatus according to the present invention prevent the abrupt change in initial pH as observed in conventional cell culture containers. By preventing such an abrupt change in pH of the medium, the initial culture conditions attain a pH equilibrium more conducive to optimal cell growth. Thus, a disadvantage of conventional cell culture containers, as opposed to the cell culture apparatus according to the present invention, is that conventional cell culture containers require a head space between the top of the container and the surface of the tissue culture medium. Additionally, in a method of culturing cells in the cell culture apparatus according to the present invention, wherein the culture chamber is filled in a manner wherein a substantial head space is lacking, the cell culture apparatus may be tilted or gently shaken to mix the medium and cells contained therein, without causing detectable foam formation or cell trauma.

In an additional embodiment of a method of culturing cells using the cell culture apparatus according to the present invention, the method comprises suspending anchorage-dependent cells to be cultured in an appropriate amount of tissue culture medium to support cell growth, in forming a suspension; introducing the suspension into a suitable instrument for injecting the suspension into the cell culture apparatus via one or more resealable apertures; using sterile (aseptic) technique, and inserting a tip of the instrument through one or more resealable apertures and into the cell culture chamber of the cell culture apparatus; expelling the suspension through the tip of the instrument and into the cell culture chamber; withdrawing the tip of instrument from the cell culture apparatus; and incubating the cell culture apparatus, containing the suspension of medium and cells, for a sufficient time (e.g., 30 minutes to 3 hours, depending on the cell type) to allow the cells to settle by gravity, and contact and attach to the membrane serving as the attachment surface. The method may further comprise subsequently rotating the cell culture apparatus 180°, and placing the cell culture apparatus in the incubator in a position so that the cells are incubated in an inverted manner in the culture chamber; i.e., the cells are attached to the membrane serving as the upper wall of the culture chamber with respect to the incubator shelf on which the cell culture apparatus rests. Hence, in this embodiment, the cells hang down into the culture chamber, and grow suspended along the surface of the upper membrane. This allows cell debris to fall by gravity, from the suspended culture, to the lower membrane where such separated cell debris may be easily removed from the culture chamber by aspiration and or a washing step.

In an illustrative example of culturing cells in the cell culture apparatus according to the present invention, and the attendant advantages, the cell growth rate (as measured by the doubling time) was calculated. In this example, in each of two tubes was mixed $1 \times 10^6$ cells of the same mammalian cell line with 20 ml of the same tissue culture medium which contained carboxyfluorescein diacetate succinimidyl ester stain ("CFSE" in a final concentration of 10 $\mu$M). CFSE is a stain that becomes incorporated internally by treated cells. The cells were allowed to incubate for 2 hours at 37° C. The CFSE-treated cells from 1 tube were introduced into the culture chamber of a cell culture apparatus according to the present invention, wherein the cells were cultured along a wall comprising a gas permeable membrane having a total surface area, onto which the cells grew, of 50 cm². The CFSE-treated cells from the second tube were introduced into a conventional tissue culture flask having a total surface area, onto which the cells grew, of 75 cm². The cell culture apparatus and the appropriately vented tissue culture flask were then incubated together at 37° C. in the same tissue culture incubator with 5% $CO_2$. As shown in Table 1, periodically the cell culture apparatus and tissue culture flask were briefly removed from the incubator, placed under a fluorescent microscope, and quantitated was the amount of fluorescence intensity of the respective cultured cells. Because the amount of dye per cell is reduced in direct proportion to the division of the cells during culture, the doubling time of the cells is represented by the time at which the fluorescence intensity of the cultured cells reaches a value representing 50% of the value of fluorescence intensity measured at the initiation of culture ("0 hour"). As shown in Table 1, and as calculated from the fluorescence intensity ("FI"), the doubling time of the cells cultured in the cell culture apparatus according to the present invention ("Device A") was 12 hours, whereas the doubling time of the cells in the conventional tissue culture flask ("Device B") was 20 hours. Additionally, the results in Table 1 show that, at least during the first 36 hours of culture, the growth rate of the cells cultured in the cell culture apparatus according to the present invention ("Device A") was unexpectedly and significantly greater than the growth rate of cells cultured in the tissue culture flask ("Device B") in the same incubation conditions.

TABLE 1

| Hours of culture | FI of cells in Device A | FI of cells in Device B |
|---|---|---|
| 0 | 40 | 40 |
| 6 | 32 | 38 |
| 12 | 20 | 30 |
| 18 | 15 | 22 |
| 24 | 11 | 17 |
| 30 | 5 | 15 |
| 36 | 0 | 11 |
| 42 | 0 | 8 |
| 48 | 0 | 4 |

TABLE 1-continued

| Hours of culture | FI of cells in Device A | FI of cells in Device B |
|---|---|---|
| 54 | 0 | 2 |
| 60 | 0 | 0 |

EXAMPLE 4

The cell culture apparatus may also be used for magnetic separation applications. In this example, illustrated are various embodiments wherein the cell culture apparatus further comprises a magnetic sheet detachably secured thereto. In one embodiment, and in referring now to FIGS. 1, 7, 9, 11, and 12, a magnetic sheet 51 is extended over and detachably secured to cell culture apparatus 12 in a face to face manner such that the magnetic sheet is placed in a position selected from the group consisting of close proximity to, or contact with, substantially all (all or that portion of the membrane which forms a wall of culture chamber 40) of the surface of membrane 31. The term "close proximity" refers to the magnetic sheet being close enough to (without physical contact with) membrane 31 such that the magnetic field is sufficiently strong enough to effect a magnetic attraction of magnetic particles to be held in position along membrane 31 in a process of magnetic separation, as will be more apparent from the following descriptions. As will be apparent to one skilled in the art, such close proximity may depend on factors that include, but are not limited to, the magnetic field strength of the magnetic sheet used, the size of the magnetic particles used in the separation process, and the thickness of membrane 31. The magnetic sheet may be detachably secured to the cell culture apparatus in a manner for magnetic particles placed within the culture chamber 40 to be attracted to, and held into position (along the inside wall of culture chamber 40 comprising the inner surface of the membrane 31) by, the magnetic field strength of the detachably secured magnetic sheet. For example, detachably securing magnetic sheet 51 to cell culture apparatus 12 may be achieved by a means selected from the group consisting of one or more fasteners, one or more clamps, a non-permanent adhesive, a sealed vacuum hold-down, a ferromagnetic material to which the magnetic sheet can bind via magnetic attractive forces, a combination thereof, or other suitable form having properties compatible with its intended purpose, as will be more apparent to one skilled in the art from the following description.

In a preferred embodiment, magnetic sheet 51 has a form generally co-dimensional with the membrane to which it is placed in contact with, and magnetic sheet 51 is detachably secured to the membrane by use of a non-permanent adhesive. The magnetic sheet can be detachably secured along and to a portion of the cell culture apparatus selected from the group consisting of the bottom of the frame, the bottom of a membrane, and a combination thereof. The non-permanent adhesive is a "removable" adhesive of a sufficiently low tack that allows the magnetic sheet to be removed from contact with the cell culture apparatus to which it is detachably secured. That is, the non-permanent adhesive is an adhesive of adequate peel strength to allow for the magnetic sheet to be pulled apart from the cell culture apparatus, without substantially damaging surfaces of either the cell culture apparatus or the magnetic sheet when they are pulled apart from each other. In a more preferred embodiment, additionally the adhesive is of an initial and appropriate cohesive strength to control and inhibit the substantial transfer of adhesive residue to a surface other than the surface onto which it is specifically layered (the latter could include one or more of the frame, the membrane in closest proximity to the magnetic sheet, or the magnetic sheet). In that regard, and in a preferred embodiment, the non-permanent adhesive is applied to the magnetic sheet, so as to avoid substantial transfer of the adhesive, or residue thereof, from interfering with the optical clarity of the membrane of the cell culture apparatus to which it is detachably secured. The non-permanent adhesive may be in the form of a double-faced adhesive tape, a polymeric adhesive, a pressure-sensitive acrylic adhesive, hot-melt adhesive, rubber cement, or any other form of adhesive useful for the purposes attendant to the present invention, as will be more apparent in the following descriptions. Double-faced adhesive tapes are known in the art to have adhesives on both sides of a film or carrier, wherein the film or carrier functions as a support onto which is applied the adhesives. In one embodiment, the non-permanent adhesive comprises a "repositionable" adhesive which allows for the magnetic sheet to be removed from the cell culture apparatus; and additionally if desired, following removal, allows for the magnetic sheet to be repositioned with respect to the cell culture apparatus, and reapplied in a detachably secured manner with the application of light pressure to the cell culture apparatus and/or magnetic sheet. Repositionable adhesives can be repeatedly adhered to and removed from a substrate without substantial loss of adhesion capacity (for a review of such adhesives, see, e.g., U.S. Pat. No. 5,663,241). Illustrative examples of a high performance pressure sensitive adhesives useful in the present invention are commercially available under the product name "MACbond IB-3628" by MACtace, Inc., Stow, Ohio; and AR-7840 by Adhesives Research, Inc.

Figure 12:
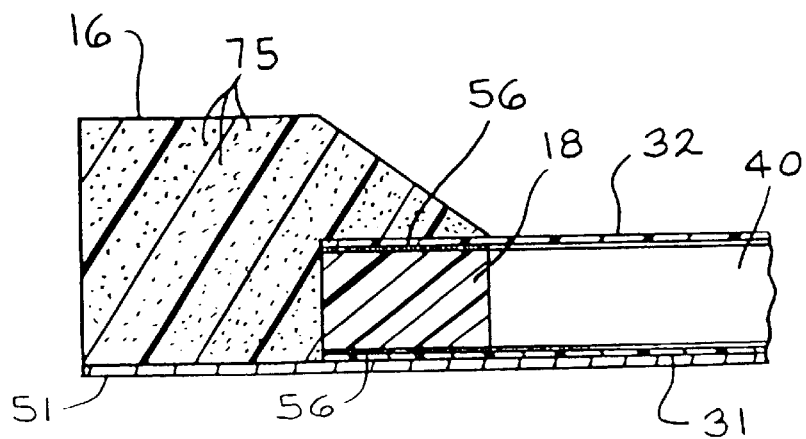
FIG. 12 is a partial cross-sectional view of a cell culture apparatus showing an embodiment wherein the outer frame contains metal particles embedded therein, and a magnetic sheet is held in position by magnetic attraction to the metal particles.

In an alternative embodiment, frame 18 and/or outer frame 16 comprises a molded plastic with ferromagnetic material embedded therein. The ferromagnetic material may comprise particles, one or more filaments, one or more wires, and the like. For purposes of illustration, frame 18 (or outer frame 16, as illustrated in FIG. 12) comprises a molded plastic with ferromagnetic particles embedded therein, wherein by magnetic attraction to such embedded particles, magnetic sheet 51 can be detachably secured to cell culture apparatus.

In a method of magnetic separation using the cell culture apparatus having detachably secured thereto a magnetic sheet, and using methods described in the previous Examples herein, introduced into the culture chamber are: (a) a fluid containing a mixed population of cells in which there is a population of target cells (e.g., the cell type desired to be isolated from the fluid containing the mixed population of cells types); and (b) a magnetic separation reagent comprising magnetic particles coated with a ligand, wherein the ligand has sufficient binding specificity and affinity for the cells desired to be separated and for achieving magnetic separation. After mixing the contents together for a sufficient time for contact and binding interactions between the magnetic separation reagent and the target cells to occur, the magnetic separation reagent contacts and binds, via the ligand coating, with target cells present in the fluid in forming complexes. It will be apparent to one skilled in the art that the fluid containing the mixed population of cells, and the magnetic separation reagent may be mixed first, and then the mixture is introduced in the cell culture apparatus for performing the magnetic separation. In either embodiment, complexes formed are drawn to (by magnetic attraction), and contact the wall of culture chamber 40 comprising the inner face of membrane 31, along the plane of cell culture apparatus to which is detachably secured the magnetic sheet. Magnetic sheet 51 is of sufficient field strength to hold the complexes (and any magnetic separation reagent not bound to cells) in position along membrane 31. As previously mentioned herein, it is noted that physical contact between membrane 31 and magnetic sheet 51 is not required for magnetic sheet 51 to hold the complexes in position along membrane 31. Further, in an embodiment wherein magnetic sheet 51 and membrane 31 are not in physical contact before the fluid and cells and magnetic separation reagent are added to cell culture apparatus 12, such components when added to culture chamber 40 may be of sufficient weight to press membrane 31 down and into contact with magnetic sheet 51.

After allowing for a sufficient time for complexes to be held into position along membrane 31, the fluid is removed from the cell culture apparatus. In a method of negative selection, the removed fluid is utilized because it has been depleted of a specific cell population. In a process of positive selection, because the cell type desired to be separated is held in position by magnetic attraction and as complexes in the culture chamber, the removed fluid contains substantially all of the (unwanted) remainder of the mixed cell populations. In this positive selection process, culture chamber 40 may be washed with a solution (e.g., tissue culture medium or physiological solution) to remove any remaining unbound cells, while the target cells remain bound, via magnetic attraction, as part of the complex with the magnetic separation reagent. In one embodiment wherein it is desired to culture the positively selected cells, the appropriate amount and type of tissue culture medium relative to that cell type is then introduced into the culture chamber; the magnetic sheet is then removed (e.g., by a pulling or peeling action) from the cell culture apparatus, thereby removing the magnetic force holding the complexes in place in the culture chamber, and thereby releasing the complexes into the medium; and then the cell culture apparatus is placed into and incubated in a cell culture incubator. Note that both the cell culture apparatus 12 and magnetic sheet 51 may be generally rectangular. However, in one embodiment the cell culture apparatus has one of the four corners of the frame cut-off, so as to facilitate gripping of an over-hanging edge of the magnetic sheet 51, in facilitating removal of magnetic sheet 51 from cell culture apparatus 12.

To illustrate a method of magnetic separation using the cell culture apparatus (which further comprises a magnetic sheet detachably secured thereto), used was a cell mixture of $1.5 \times 10^6$ T47-D (human breast carcinoma cell line which is relatively slow growing) and $1.5 \times 10^6$ Jurkat cells (human T cell line). A commercially available magnetic reagent comprising magnetic beads with an anti-epithelial cell marker antibody (BER-EP4) attached thereto was mixed for 30 minutes by agitation with the cell mixture at an approximate ratio of 6 beads per cell in a small tube in an approximate total volume of 500 $\mu$l. The mixture comprising the cells and magnetic reagent was then introduced into the cell culture apparatus containing 19.5 ml of tissue culture medium with mixing, and then a magnetic sheet having a field strength of 525 Gauss was detachably secured to the cell culture apparatus along the membrane which formed the bottom wall of the culture chamber. The cell culture apparatus having the magnetic sheet detachably secured thereto was placed on a rotating platform for 10 minutes, and then the tissue culture medium was removed from the cell culture apparatus. The removed tissue culture medium, and its cell content, were placed into a separate container, and were a result of a negative selection process. While optionally a wash step may be performed in a positive selection process, in this example a wash step was not performed. Rather, the magnetic sheet was removed from the cell culture apparatus, 20 ml of tissue culture medium was added to and mixed with the cells positively selected for in the cell culture apparatus, and then the cell culture apparatus was incubated at 37° C. for 1 week in a 5% $CO_2$ incubator. After 1 week of culture, anchorage-dependent cells (harvested by trypsinization) and anchorage-independent cells in the culture were collected, stained with anti-CD45 antibody labeled with phycoerythrin (for detecting Jurkat cells) and with antepithelial cell marker antibody labeled with fluorescein isothiocyanate (for detecting T47-D cells), and analyzed and quantitated by flow cytometry. The amount of each cell type detected in the culture was then expressed as a percentage of the total cell count of the culture. As shown in Table 2, the results of three independent experiments of using the cell culture apparatus further comprising a magnetic sheet detachably secured thereto in a positive selection process showed an efficiency of positive selection of greater than 99%. Note that while optionally, in culturing positively-selected cells the magnetic beads may be first removed before culturing, in this example the positively selected cells were still bound to the magnetic beads at the initiation of culture.

TABLE 2

Positive selection

| Experiment # | Cell Count | Jurkat cells | T47-D cells |
|---|---|---|---|
| 1 | $3.9 \times 10^6$ | 0.25% | 99.55% |
| 2 | $5.4 \times 10^6$ | 0.40% | 99.30% |
| 3 | $5.1 \times 10^6$ | 0.20% | 99.65% |

To the cells separated by negative selection were also cultured for 1 week, harvested, and stained for and analyzed by flow cytometry using the methods described herein. The amount of each cell type detected in the culture was then expressed as a percentage of the total cell count of the culture. As shown in Table 3, the results of three independent experiments of using the cell culture apparatus further comprising a magnetic sheet detachably secured thereto in a negative selection process showed an efficiency of negative selection of about 95% or greater than 95%.

TABLE 3

Negative selection

| Experiment # | Cell Count | Jurkat cells | T47-D cells |
|---|---|---|---|
| 1 | $1.8 \times 10^6$ | 95.0% | 5.0% |
| 2 | $7.0 \times 10^6$ | 98.5% | 1.5% |
| 3 | $2.3 \times 10^6$ | 94.9% | 2.6% |

EXAMPLE 5

The cell culture apparatus according to the present invention may also be used for applications in which recombinant DNA molecules are introduced into cultured cells. In this example, illustrated is the use of the cell culture apparatus in which a vector is introduced into the cells by introducing an effective amount of the vector (for introduction into the cultured cells) into the cell culture apparatus so that the vector contacts the cultured cells contained in the culture chamber of the cell culture apparatus. The methods used for introducing a substance into the cell culture apparatus, as described in Example 3 herein, may also be used to introduce the vector into the cell culture apparatus. As will be apparent to one skilled in the art, the vector may comprise a plasmid vector, viral vector, expression vector, or a combination thereof. As apparent to one skilled in the art, the vector may comprise a recombinant. DNA molecule comprising the vector operatively linked (e.g., to a promoter) to a desired DNA molecule to be expressed by cells containing the vector. As known to those skilled in the art of molecular biology, animal cells (and more preferably, mammalian cells) or plant cells are typical cells into which it is desired to introduce a recombinant DNA molecule such as an expression vector for promoting expression of a desired gene into a gene product in the cells.

For example, cultured cells contained in the cell culture apparatus may be incubated with a mixture comprising an amount of a recombinant DNA molecule desired to be introduced into the cells, and a transfection reagent. As an illustrative example, a commercially available plasmid ("pTracer") which encodes a green fluorescent protein was introduced into cells cultured in the cell culture apparatus by transfection. In this example, the cell culture apparatus was seeded with $1 \times 10^6$ T47-D cells and allowed to grow until the cells were approximately 50–60% confluent with respect to the attachment surface. In a small tube was mixed 500 µg of plasmid DNA and 900 µl of serum-free tissue culture medium. In another tube was mixed 120 µl of a commercially available, lipid-containing, transfection reagent, and 600 µl of tissue culture medium. After a 30 minute room temperature incubation, the contents of the two tubes were mixed, and the mixture was incubated for 10 minutes. The mixture was the further mixed with 18 ml of tissue culture medium. After removing the tissue culture medium from the cell culture apparatus, and washing the cultured cells once with medium, the mixture comprising the tissue culture medium and transfection reagent and vector was introduced through the aperture and expelled into the culture chamber so as to contact the adherent, cultured cells. The cell culture apparatus was then incubated overnight at 37° C. in 5% $CO_2$ so that the contact between the cultured cells and the mixture (comprising the tissue culture medium and transfection reagent and vector) promoted the uptake by and introduction into cultured cells of the vector. The tissue culture medium was then removed from the cell culture apparatus, and replaced with tissue culture medium which lacked phenol red as a pH indicator. The cell culture apparatus was then placed onto the stage of a ultraviolet light microscope and the cultured cells were analyzed and quantitated for fluorescence produced by the expressed green fluorescent protein. The number of cells positive for the green fluorescence and the total number of cells in the culture were quantitated to determine the percentage of cells that were successfully transfected ("transfection efficiency"). The resultant transfection efficiency was about 20%. As will be apparent to one skilled in the art, the transfection efficiency may be increased depending on factors which include, but are not limited to, the type of cells into which it is desired to introduce the vector, optimization of the conditions for transfection (e.g., the amount of DNA per number of cells, the medium used for transfection, the time of the transfection process), and the type and amount of transfection reagent used. Also, it will be apparent to one skilled in the art that using similar steps, a vector may also be introduced into anchorage-independent cells cultured in the cell culture apparatus according to the present invention.

The foregoing description of the specific embodiments of the present invention have been described in detail for purposes of illustration. In view of the descriptions and illustrations, others skilled in the art can, by applying, current knowledge, readily modify and/or adapt the present invention for various applications without departing from the basic concept; and thus, such modifications and/or adaptations are intended to be within the meaning and scope of the appended claims.

What is claimed is:

1. A cell culture apparatus comprising:
    a frame comprising a housing, and at least one aperture which comprises an opening through the frame, wherein the at least one aperture is resealable;
    two membranes, wherein each membrane comprises a gas permeable membrane, wherein the membranes are securedly sealed in a leak-proof sealing to the frame in forming a culture chamber between the two membranes and the frame, and wherein the membranes are of a sufficient optical transparency and clarity so as to permit observation of a cell culture.

2. The cell culture apparatus according to claim 1, wherein the frame comprises 2 or more resealable apertures.

3. The cell culture apparatus according to claim 1, wherein at least one of the membranes comprises a surface treated to improve cell attachment.

4. The cell culture apparatus according to claim 1, wherein the cell culture comprise cells selected from the group consisting of individual cells, cells forming a tissue, and a combination thereof.

5. The cell culture apparatus according to claim 1, wherein the cell culture apparatus is generally rectangular in shape.

6. The cell culture apparatus according to claim 1, wherein the cell culture apparatus has a length in the range of from about 10 centimeters (cm) to about 13.5 cm, a width in a range of from about 7 cm to about 9 cm, and a height in a range of from about 0.2 cm to about 2 cm.

7. The cell culture apparatus according to claim 6, wherein the two membranes are spaced apart by a distance in the range of from about 1 millimeter (mm) to about 5 mm.

8. The cell culture apparatus according to claim 1, wherein the frame further comprises scoring cuts which may be used to break the frame along the scoring cuts.

9. The cell culture apparatus according to claim 1, wherein each aperture comprises a self-sealing gasket material in forming a resealable aperture.

10. The cell culture apparatus according to claim 1, wherein an adhesive is interdispersed and cured between each membrane and the frame in providing a leak-proof sealing.

11. A cell culture apparatus comprising:
    a frame comprising a housing, and at least one aperture which comprises an opening through the frame, wherein the at least one aperture is resealable;
    two membranes, wherein at least one of the membranes comprises a gas permeable membrane, wherein the membranes are securedly sealed in a leak-proof sealing to the frame in forming multiple culture chambers between the two membranes and the frame, wherein each of the multiple culture chambers is accessible by at least one resealable aperture, and wherein the membranes are of a sufficient optical transparency and clarity so as to permit observation of a cell culture.

12. The cell culture apparatus according to claim 11, further comprising an outer frame comprising a housing into which is fitted and secured the frame of claim 11, wherein the outer frame comprises at least one aperture which is aligned and contacted in a leak proof sealing with an aperture of the frame of claim 11 in forming an aligned aperture, and wherein at least one aperture of the aligned apertures comprises a resealable aperture.

13. The cell culture apparatus according to claim 12, wherein the frame of claim 11 is fitted into and secured to a recessed portion of the outer frame.

14. The cell culture apparatus according to claim 12, wherein the outer frame comprises a beveled portion which slopes at a 35° angle in relation to the plane of the at least one gas permeable membrane.

15. The cell culture apparatus according to claim 11, wherein the frame comprises 2 or more resealable apertures.

16. The cell culture apparatus according to claim 11, wherein a first of the two membranes comprises a gas permeable membrane, and a second of the two membranes comprises a non-permeable membrane.

17. The cell culture apparatus according to claim 11, wherein each of the two membranes comprises a gas permeable membrane.

18. The cell culture apparatus according to claim 11, wherein the at least one gas permeable membrane comprises a surface treated to improve cell attachment.

19. The cell culture apparatus according to claim 11, wherein the cell culture comprises cells selected from the group consisting of individual cells, cells forming a tissue, and a combination thereof.

20. The cell culture apparatus according to claim 11, wherein the cell culture apparatus is generally rectangular in shape.

21. The cell culture apparatus according to claim 11, wherein the cell culture apparatus has a length in the range of from about 10 centimeters (cm) to about 13.5 cm, a width in a range of from about 7 cm to about 9 cm, and a height in a range of from about 0.2 cm to about 2 cm.

22. The cell culture apparatus according to claim 21, wherein the two membranes are spaced apart by a distance in the range of from about 1 millimeter (mm) to about 5 mm.

23. The cell culture apparatus according to claim 11, wherein the frame further comprises scoring cuts which may be used to break the frame along the scoring cuts.

24. The cell culture apparatus according to claim 11, wherein each aperture comprises a self-sealing gasket material in forming a resealable aperture.

25. The cell culture apparatus according to claim 11, wherein an adhesive is interdispersed and cured between each membrane and the frame in providing a leak-proof sealing.

26. A cell culture apparatus comprising:
    a frame comprising a housing, and at least one aperture which comprises an opening through the frame, wherein the at least one aperture is resealable;
    two membranes, wherein at least one of the membranes comprises a gas permeable membrane, wherein the membranes are securedly sealed in a leak-proof sealing to the frame in forming a culture chamber between the two membranes and the frame, and wherein the membranes are of a sufficient optical transparency and clarity so as to permit observation of a cell culture; and
    a magnetic sheet extended over and detachably secured to the cell culture apparatus in a face to face manner, wherein the magnetic sheet is in a position selected from the group consisting of close proximity to, and in contact with, a membrane which forms the culture chamber of the cell culture apparatus.

27. The cell culture apparatus according to claim 26, wherein the magnetic sheet is detachably secured by a means selected from the group consisting of one or more fasteners, one or more clamps, a non-permanent adhesive, a sealed vacuum hold-down, a ferromagnetic material to which the magnetic sheet can bind via magnetic attractive forces, and a combination thereof.

28. The cell culture apparatus according to claim 26, wherein the magnetic sheet is detachably secured to a portion of the cell culture apparatus selected from the group consisting of the frame, the membrane, and a combination thereof.

29. The cell culture apparatus according to claim 12, wherein the cell culture apparatus further comprises a magnetic sheet detachably secured thereto, wherein the magnetic sheet is extended over and detachably secured to cell culture apparatus in a face to face manner by placing the magnetic sheet in a position selected from the group consisting of close proximity to, and in contact with, a membrane which forms the culture chamber of the cell culture apparatus.

30. The cell culture apparatus according to claim 29, wherein the magnetic sheet is detachably secured by a means selected from the group consisting of one or more fasteners, one or more clamps, a non-permanent adhesive, a sealed vacuum hold-down, a ferromagnetic material to which the magnetic sheet can bind via magnetic attractive forces, and a combination thereof.

31. The cell culture apparatus according to claim 29, wherein the magnetic sheet is detachably secured to a portion of the cell culture apparatus selected from the: group consisting of a frame, the membrane, and a combination thereof.

32. The cell culture apparatus according to claim 26, wherein the frame comprises 2 or more resealable apertures.

33. The cell culture apparatus according to claim 26, wherein a first of the two membranes comprises a gas permeable membrane, and a second of the two membranes comprises a non-permeable membrane.

34. The cell culture apparatus according to claim 26, wherein each of the two membranes comprises a gas permeable membrane.

35. The cell culture apparatus according to claim 26, wherein the at least one gas permeable membrane comprises a surface treated to improve cell attachment.

36. The cell culture apparatus according to claim 26, further comprising cells selected,from the group consisting of individual cells, cells forming a tissue, and a combination thereof.

37. The cell culture apparatus according to claim 26, wherein the cell culture apparatus is generally rectangular in shape.

38. The cell culture apparatus according to claim 26, wherein the cell culture apparatus has a length in the range of from about 10 centimeters (cm) to about 13.5 cm, a width in a range of from about 7 cm to about 9 cm, and a height in a range of from about 0.2 cm to about 2 cm.

39. The cell culture apparatus according to claim 26, wherein the two membranes are spaced apart by a distance in the range of from about 1 millimeter (mm) to about 5 mm.

40. The cell culture apparatus according to claim 26, wherein the frame further comprises scoring cuts which may be used to break the frame along the scoring cuts.

41. The cell culture apparatus according to claim 26, wherein each aperture comprises a self-sealing gasket material in forming a resealable aperture.

42. The cell culture apparatus according to claim 26, wherein an adhesive is interdispersed and cured between each membrane and the frame in providing a leak-proof sealing.

43. A bioreactor comprising a plurality of cell culture apparatuses, wherein a fluid passageway is provided between the plurality of cell culture apparatuses, wherein the fluid passageway allows for fluid flow communication between culture chambers of cell culture apparatuses connected by the fluid passageway, and wherein a cell culture apparatus comprises:

a frame comprising a housing, and at least one aperture which comprises an opening through the frame, wherein the at least one aperture is resealable;

two membranes, wherein at least one of the membranes comprises a gas permeable membrane, wherein the membranes are securedly sealed in a leak-proof sealing to the frame in forming a culture chamber between the two membranes and the frame, and wherein the membranes are of a sufficient optical transparency and clarity so as to permit observation of a cell culture.

44. A method of culturing cells in the cell culture apparatus according to claim 1, the method comprising:

(a) suspending the cells to be cultured in an appropriate amount of tissue culture medium to support cell growth, in forming a suspension;

(b) introducing the suspension into an instrument for injecting the suspension into the cell culture apparatus;

(c) inserting a portion of the instrument through a resealable aperture and into the cell culture chamber of the cell culture apparatus;

(d) expelling the suspension from the instrument and into the cell culture chamber;

(e) withdrawing the portion of the instrument from the cell culture apparatus; and (f) incubating the cell culture apparatus, containing the suspension of medium and cells, in a cell culture incubator.

45. The method according to claim 44, further comprising a venting step after step (d) to remove air which is expelled into the culture chamber during step (d).

46. The method according to claim 44, wherein the cells to be cultured are anchorage-dependent cells.

47. The method according to claim 44, wherein the cells to be cultured are anchorage-independent cells.

48. The method according to claim 46, wherein after the anchorage-dependent cells have attached to a membrane of the cell culture apparatus in step (f), the method comprises a further step of rotating the cell culture apparatus 180° in culturing the cells in an inverted manner in the culture chamber.

49. The method according to claim 46, wherein after the anchorage-dependent cells have attached to a membrane of the cell culture apparatus in step (f), the method comprises the further steps:

(g) rotating the cell culture apparatus 180°; and (h) repeating steps (c) through (f);

wherein each of the two membranes serves an attachment surface onto which cells are cultured.

50. A method of culturing cells in the cell culture apparatus according to claim 11, the method comprising:

(g) suspending the cells to be cultured in an appropriate amount of tissue culture medium to support cell growth, in forming a suspension;

(h) introducing the suspension into an instrument for injecting the suspension into the cell culture apparatus;

(i) inserting a portion of the instrument through a resealable aperture and into at least one cell culture chamber of the cell culture apparatus;

(j) expelling the suspension from the instrument and into the at least one cell culture chamber;

(k) withdrawing the portion of the instrument from the cell culture apparatus; and (l) incubating the cell culture apparatus, containing the suspension of medium and cells, in a cell culture incubator.

51. The method according to claim 50, further comprising a venting step after step (d) to remove air which is expelled into the at least one culture chamber during step (d).

52. The method according to claim 50, wherein the cells to be cultured are anchorage-dependent cells.

53. The method according to claim 50, wherein the cells to be cultured are anchorage-independent cells.

54. A method of culturing cells in the cell culture apparatus according to claim 12, the method comprising:

(a) suspending the cells to be cultured in an appropriate amount of tissue culture medium to support cell growth, in forming a suspension;

(b) introducing the suspension into an instrument for injecting the suspension into the cell culture apparatus;

(c) inserting a portion of the instrument through aligned apertures and into the cell culture chamber of the cell culture apparatus;

(d) expelling the suspension from the instrument and into the cell culture chamber;

(e) withdrawing the portion of the instrument from the cell culture apparatus; and (f) incubating the cell culture apparatus, containing the suspension of medium and cells, in a cell culture incubator.

55. The method according to claim 54, further comprising a venting step after step (d) to remove air which is expelled into the culture chamber during step (d).

56. The method according to claim 54, wherein the cells to be cultured are anchorage-dependent cells.

57. The method according to claim 54, wherein the cells to be cultured are anchorage-independent cells.

58. The method according to claim 56, wherein after the anchorage-dependent cells have attached to a membrane of the cell culture apparatus in step (f), the method comprises a further step of rotating the cell culture apparatus 180° in culturing the cells in an inverted manner in the culture chamber.

59. The method according to claim 56, wherein after the anchorage-dependent cells have attached to a membrane of the cell culture apparatus in step (f), the method comprises the further steps:

(g) rotating the cell culture apparatus 180°; and (h) repeating steps (c) through (f);

wherein each of the two membranes serves an attachment surface on which cells are cultured.

60. A method of magnetic separation using the cell culture apparatus according to claim 26, the method comprising:

(a) mixing a fluid containing a mixed population of cells in which there is a population of a cell type desired to be isolated by magnetic separation together with a magnetic separation reagent having binding specificity for the cell type desired to be separated, in forming a mixture comprising complexes between the magnetic separation reagent and cells of the type for which it has binding specificity;

(b) introducing the mixture into the culture chamber of the cell culture apparatus so that the mixture contacts a wall of the culture chamber formed by a membrane, along the plane of which is detachably secured the magnetic sheet; and (c) incubating the mixture in the cell culture apparatus for a sufficient time for the complexes to contact and be held in position along the wall of the culture chamber due to attraction of the complexes to a magnetic field strength of the magnetic sheet.

61. The method according to claim 60, further comprising removing from the cell culture apparatus the mixture which remains unbound in the culture chamber, and wherein the removed mixture comprises cells separated by a process of negative selection.

62. The method according to claim 61, wherein after removal of the mixture, the cells comprising the complexes bound in the culture chamber and which remain in the cell culture apparatus comprise cells separated by a process of positive selection.

63. The method according to claim 62, further comprising introducing tissue culture medium into the culture chamber, removing the magnetic sheet from the cell culture apparatus, and incubating the cell culture apparatus in culturing the cells separated by the process of positive selection.

64. A method of introducing a recombinant DNA molecule into cells cultured in a cell culture apparatus, the method. comprising:

(a) mixing a transfection reagent with the recombinant DNA molecule comprising a vector in forming a mixture comprising the recombinant DNA molecule;

(b) mixing the mixture comprising the recombinant DNA molecule with tissue culture medium in forming medium comprising the recombinant DNA molecule;

(c) introducing the medium comprising the recombinant DNA molecule into the culture chamber so as to contact the cultured cells in the cell culture apparatus; and (d) incubating the medium comprising the recombinant DNA molecule in contact with the cultured cells in promoting introduction of the recombinant DNA molecule into cultured cells in the culture chamber;

wherein the cell culture apparatus comprises (i) a frame comprising a housing, and at least one aperture which comprises an opening through the frame, wherein the at least one aperture is resealable, and (ii) two membranes, wherein at least one of the membranes comprises a gas permeable membrane, wherein the membranes are securely sealed in a leak-proof sealing to the frame in forming a cell culture chamber between the two membranes and the frame, and wherein the membranes are of a sufficient optical transparency and clarity so as to permit observation of the cell culture.

* * * * *